United States Patent
Archambeau et al.

(10) Patent No.: US 10,563,120 B2
(45) Date of Patent: Feb. 18, 2020

(54) ELECTROCHROMIC COMPOUNDS AND OPTICAL ARTICLES CONTAINING THEM

(71) Applicant: Essilor International, Charenton le Pont (FR)

(72) Inventors: Samuel Archambeau, Charenton-le-Pont (FR); Claudine Biver, Charenton-le-Pont (FR); Fabien Berit-Debat, Charenton-le-Pont (FR); Stuart Aiken, York (GB); Christopher David Gabbutt, Preston (GB); Bernard Mark Heron, Brough (GB); Thomas David Broadbent, Huddersfield (GB)

(73) Assignee: Essilor International, Charenton le Pont (FR)

( * ) Notice: Subject to any disclaimer, the term of this patent is extended or adjusted under 35 U.S.C. 154(b) by 0 days.

(21) Appl. No.: 15/742,085

(22) PCT Filed: Jul. 6, 2016

(86) PCT No.: PCT/EP2016/066052
§ 371 (c)(1),
(2) Date: Jan. 5, 2018

(87) PCT Pub. No.: WO2017/005824
PCT Pub. Date: Jan. 12, 2017

(65) Prior Publication Data
US 2018/0194995 A1    Jul. 12, 2018

(30) Foreign Application Priority Data
Jul. 8, 2015  (EP) ..................... 15306123

(51) Int. Cl.
| | | |
|---|---|---|
| C07D 213/06 | (2006.01) |
| C07D 213/26 | (2006.01) |
| C07D 213/22 | (2006.01) |
| C09K 9/02 | (2006.01) |
| G02F 1/1503 | (2019.01) |
| G02F 1/153 | (2006.01) |

(52) U.S. Cl.
CPC .............. *C09K 9/02* (2013.01); *C07D 213/06* (2013.01); *C07D 213/22* (2013.01); *C07D 213/26* (2013.01); *G02F 1/1503* (2019.01); *G02F 1/1533* (2013.01); *C09K 2211/1007* (2013.01); *C09K 2211/1011* (2013.01); *C09K 2211/1018* (2013.01); *G02F 2202/02* (2013.01)

(58) Field of Classification Search
CPC .... C07D 213/06; C07D 213/26; C07D 213/22
USPC ......................................................... 546/255
See application file for complete search history.

(56) References Cited

FOREIGN PATENT DOCUMENTS

| | | | |
|---|---|---|---|
| DE | 102012201673 | * | 8/2013 |
| JP | 2009-48141 A | | 3/2009 |
| JP | 2015-124228 A | | 7/2015 |

OTHER PUBLICATIONS

Samanta, D et al., Chem. Comm. 2014, vol. 50, 1595-1598.*
International Search Report dated Sep. 1, 2016 in PCT/EP2016/066052 filed Jul. 6, 2016.
Zhenfu Han et al., "Hexakis(4-(N-butylpyridylium))benzene: A Six-Electron Organic Redox System", The Journal of Organic Chemistry, 2008, vol. 73, No. 2, pp. 445-450, XP055227499.
Andrew Pun et al., "Facile Route to an All-Organic, Triply Threaded, Interlocked Structure by Templated Dynamic Clipping", Angewandte Chemie International Edition, 2012, vol. 51, No. 52, pp. 13119-13122, XP055227511.
Guoming Wang et al., "Synthesis, electrochemical and electrochromic properties of novel pyridinium salts based on 2,6-di(4-pyndyl)-4-benzylpyridilium", Chemical Physics Letters, Aug. 20, 2014, vol. 614, pp. 243-250, XP029078860.
Michael Neumann-Spallart et al., "Stable Water Insoluble Radicals of 1,1'',1'''-tribenzyl[4,2'; 4',4''; 6',4''']quaterpyridinium Trichloride for Photochromic Films", Materials Express, 2011, vol. 1, No. 4, pp. 350-354, XP055246401.
Dirk Bongard et al., "Synthesis of Nonsymmetrically N,N'-Diaryl-Substituted 4,4'-Bipyridinium Salts with Redox-Tunable and Titanium Dioxide (TiO$_2$)-Anchoring Properties", Helvetica Chimica Acta, 2005, vol. 88, pp. 3200-3209, XP055246412.

* cited by examiner

*Primary Examiner* — Niloofar Rahmani
(74) *Attorney, Agent, or Firm* — Oblon, McClelland, Maier & Neustadt, L.L.P.

(57) ABSTRACT

Electrochromic compounds and optical articles containing them The present invention relates to a group of novel electrochromic compounds. More specifically, it relates to electrochromic compounds comprising one or several pyridinium rings and the use of these compounds as a variable transmittance medium for the manufacture of an optical article, such as an ophthalmic lens.

15 Claims, No Drawings

ELECTROCHROMIC COMPOUNDS AND OPTICAL ARTICLES CONTAINING THEM

The present invention relates to a group of novel electrochromic compounds. More specifically, it relates to electrochromic compounds comprising one or several pyridinium rings and the use of these compounds as a variable transmittance medium for the manufacture of an optical article, such as an ophthalmic lens.

Electrochromism is a well known physical phenomenon which is observed with certain classes of chemical compounds that reversibly change colour when a voltage is applied to them. The material undergoes reversible changes in optical properties by oxidation and reduction. Advantageously, the electrochromic material is colourless when an electric field is not applied and becomes coloured when an electric field is applied.

An electrochromic device, i.e. a device containing electrochromic compounds, the absorbance of which depends only on the presence of an electric field, can thus have two states, i.e. a coloured state (when electrically activated) and a bleached state (in the inactive state). The optical transmission properties of the device depend on the nature of the electrochromic compounds.

There remains a need for improving electrochromic materials in order to use them as transparent media for forming high quality articles, in particular high quality ophthalmic lenses, while keeping electrochromic properties and having a wide range of colours.

Compounds comprising several pyridinium rings are known to be good candidates for electrochromic materials. The challenge with compounds comprising several pyridinium rings is that they may exhibit two reduction peaks, the second reduction process being known to generate species having solubility and/or stability issues. For example, bipyridinium (bipm) compounds may exhibit three oxidation states: $V^{2+}$ (bipm$^{2+}$), $V^{+}$ (bipm$^{+}$) and $V^{0}$ (bipm$^{0}$), as shown in the scheme below:

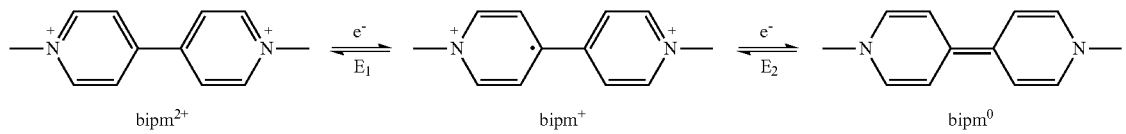

The reduction of $V^{2+}$ to $V^{+}$ occurs at potential $E_1$ and is reversible. However, the reduction of $V^{+}$ to $V^{0}$ that occurs at potential $E_2$ is often less reversible, in part because $V^{0}$ is frequently an insoluble species. Indeed, when $V^{0}$ is soluble it is known to be reactive, undergoing oxidation and participating in photochemical reactions to afford non-electrochromic impurities. Additionally, the species $V^{0}$ has a different visible absorption spectrum to $V^{+}$ which is problematic in variable transmission applications. Furthermore, the presence of $V^{0}$ leads to complications in electrochemical switching due to comproportionation reactions.

After conducting extensive research, the present inventors provide novel electrochromic compounds comprising one or several pyridinium groups that exhibit excellent electrochromic properties and that can be easily incorporated in a cell to form, for instance, an electrochromic lens. As such, the compounds of the present invention are advantageously:
- colourless in their inactivated state and coloured, for example green, red, purple, blue, yellow or brown, in their activated state;
- reversibly oxidized or reduced;
- easily activated, i.e. they have an electrochemical potential from −1.5 to −0.5 V;
- stable, i.e. no generation of degradation products (only one reversible oxidation peak or two peaks separated by at least 0.1V, preferably at least 0.3 V, more preferably at least 0.4 V, even more preferably at least 0.5 V).

The present invention thus relates to electrochromic compounds of formula (I) as defined below.

The present invention also relates to an electrochromic composition comprising at least one compound of formula (I).

Finally, the present invention relates to an electrochromic device, such as an ophthalmic lens, comprising an electrochromic compound of formula (I) or an electrochromic composition according to the invention.

Definitions

The expression "$C_6$-$C_{10}$ arylene" represents any divalent radical of an aromatic hydrocarbon comprising 6 to 10 carbon atoms. Examples of $C_6$-$C_{10}$ arylene groups include phenylene and naphthylene.

The expression "pyridinediyl radical" represents any divalent radical of a pyridine which is an aromatic group comprising 5 carbon atoms and a nitrogen.

The expression "pyridiniumyl radical" represents any divalent radical of a pyridinium which is an aromatic group comprising 5 carbon atoms and a positively charged nitrogen.

The expression "alkyl" represents any monovalent radical of a linear or branched hydrocarbon chain comprising 1 to 18 carbon atoms. The expression "$C_3$-$C_{18}$ alkyl" represents an alkyl group having 3 to 18 carbon atoms. The expression "$C_6$-$C_7$ alkyl" represents an alkyl group having 6 or 7 carbon atoms. Examples of $C_1$-$C_{18}$ alkyl groups include $C_1$-$C_4$ alkyl groups such as methyl, ethyl, n-propyl, i-propyl, n-butyl, i-butyl, s-butyl or t-butyl, $C_6$-$C_8$ alkyl groups such as n-hexyl, n-heptyl or n-octyl, as well as n-pentyl, 2-ethylhexyl, 3,5,5-trimethylhexyl, n-nonyl, n-decyl, n-undecyl, n-dodecyl or n-octadecyl.

The expression "N-alkylpyridinium group" represents any radical of a pyridinium which is an aromatic group comprising 5 carbon atoms and a positively charged nitrogen, said nitrogen being substituted by an alkyl group.

The expression "alkoxy" represents a radical of formula —OR wherein R is a $C_1$-$C_{12}$ alkyl. Examples of $C_1$-$C_{12}$ alkoxy groups include $C_1$-$C_6$ alkoxy groups such as —OCH$_3$, —OCH$_2$CH$_3$ or —O(CH$_2$)$_5$CH$_3$.

The expression "alkylthio" represents a radical of formula —SR wherein R is a $C_1$-$C_{12}$ alkyl. Examples of $C_1$-$C_{12}$ alkylthio groups include —SCH$_3$ and —SCH$_2$CH$_3$.

The expression "haloalkyl" represents any $C_1$-$C_{12}$ alkyl group substituted by one or more halogen atom such as F or Cl. Examples of $C_1$-$C_{12}$ haloalkyl groups include $C_1$-$C_{12}$ perhaloalkyl groups, in particular $C_1$-$C_4$ perhaloalkyl groups such as —CF$_3$, as well as C$_1$-C$_{12}$ (perhaloalkyl)alkyl groups, in particular (C$_1$-C$_4$ perhaloalkyl)-(C$_1$-C$_4$ alkyl) groups such as —CH$_2$CF$_3$.

The expression "haloalkoxy" represents a radical of formula —OR wherein R is a C$_1$-C$_{12}$ haloalkyl. Examples of C$_1$-C$_{12}$ haloalkoxy include C$_1$-C$_{12}$ perhaloalkoxy groups, in particular C$_1$-C$_4$ perhaloalkoxy groups such as —OCF$_3$, as well as C$_1$-C$_{12}$ (perhaloalkyl)alkoxy groups, in particular (C$_1$-C$_4$ perhaloalkyl)-(C$_1$-C$_4$ alkoxy) groups such as —OCH$_2$CF$_3$.

The expression "haloalkylthio" represents a radical of formula —SR wherein R is a C$_1$-C$_{12}$ haloalkyl. Examples of C$_1$-C$_{12}$ haloalkoxy groups include C$_1$-C$_{12}$ perhaloalkylthio groups, in particular C$_1$-C$_4$ perhaloalkylthio groups such as —SCF$_3$, as well as C$_1$-C$_{12}$ (perhaloalkyl)alkylthio groups, in particular (C$_1$-C$_4$ perhaloalkyl)-(C$_1$-C$_4$ alkylthio) groups such as —SCH$_2$CF$_3$.

The expression "polyalkylenoxy" represents a radical of formula —O(R'O)$_m$R wherein R' is a C$_1$-C$_{12}$ alkylene, R is a C$_1$-C$_{12}$ alkyl and m is an integer from 1 to 12. Examples of poly(C$_1$-C$_{12}$ alkylenoxy) groups include OCH$_2$CH$_2$OCH$_3$.

The expression "alkoxycarbonyl" represents a radical of formula —C(O)OR wherein R is a C$_1$-C$_{18}$ alkyl group. Examples of alkoxycarbonyl groups possessing a C$_1$-C$_{18}$ chain include —C(O)OCH$_3$ and —C(O)OC$_2$H$_5$.

The expression "aryl" represents any monovalent radical of an aromatic hydrocarbon comprising 6 to 18 carbon atoms. Examples of C$_6$-C$_{18}$ aryl groups include phenyl, naphthyl, anthracenyl and phenanthrenyl.

The expression "heteroaryl" represents any monovalent radical of a monocyclic or bicyclic 5 to 10 membered aromatic group comprising from 1 to 3 heteroatoms independently selected from oxygen, nitrogen and sulfur. Examples of C$_5$-C$_{10}$ heteroaryl groups include furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl, 1,2-benzisothiazolyl, 2,1-benzisothiazolyl, benzothiazolyl, benzoxazolyl, benzotriazolyl, pyridyl, pyridinium, quinolinyl, quinolinium, isoquinolinyl, isoquinolinium, pyridazinyl, cinnolinyl, phthalazinyl, pyrimidinyl, quinazolinyl, pyrazinyl and quinoxalinyl.

Unless mentioned otherwise, the groups and radicals defined hereinabove may be unsubstituted or substituted by one or more substituents such as, for example, halogen, alkyl, alkoxy, aryl, heteroaryl, haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino.

Electrochromic Compounds

The electrochromic compounds of the present invention have a central core (represented as Z in formula (I) below), which is either a C$_6$-C$_{10}$ arylene, a pyridineyl radical or a pyridiniumyl radical, onto which are branched two lateral pyridines or pyridiniums (which are represented as rings A and B in formula (I) below).

As such, the electrochromic compounds of the present invention are represented by formula (I):

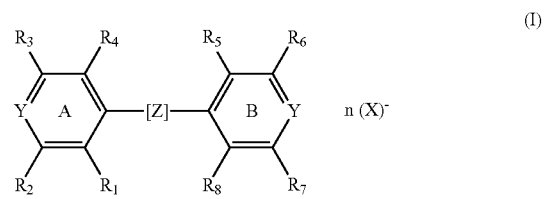

wherein:
Z is a C$_6$-C$_{10}$ arylene, a pyridinediyl radical or a pyridiniumyl radical;
each Y is independently selected from N or ($^+$N—R$_9$)(X$^-$) with R$_9$ a C$_3$-C$_{18}$ alkyl, a N-alkylpyridinium group or an aryl;
each one of R$_1$-R$_8$ is independently selected from H, alkyl, alkoxy, alkylthio, haloalkyl, haloalkoxy, haloalkylthio, polyalkylenoxy, alkoxycarbonyl, aryl or heteroaryl;
n is 1, 2, 3 or 4;
X$^-$ is a counterion.

More preferably, the electrochromic compounds of the present invention are represented by formula (I):

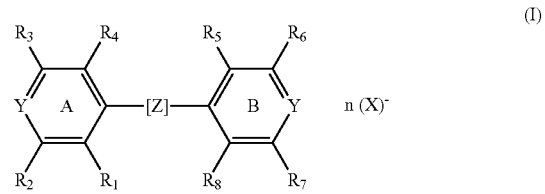

wherein:
Z is an unsubstituted phenylene, an unsubstituted naphtylene, an unsubstituted pyridinediyl radical, a substituted pyridiniumyl radical or fused pyridiniumyl radical;
each Y is independently selected from N or ($^+$N—R$_9$)(X$^-$) with R$_9$ a C$_3$-C$_{18}$ alkyl, a N-alkylpyridinium group or an aryl;
each one of R$_1$-R$_8$ is independently selected from H, alkyl, alkoxy, alkylthio, haloalkyl, haloalkoxy, haloalkylthio, polyalkylenoxy, alkoxycarbonyl, aryl or heteroaryl;
n is 1, 2, 3 or 4;
X$^-$ is a counterion.

In a first embodiment of the present invention, the central core Z of the compound of formula (I) is a C$_6$-C$_{10}$ arylene. Said C$_6$-C$_{10}$ arylene may be selected from:
ortho-branched phenylene;
meta-branched phenylene;
para-branched phenylene; or
2,6-branched naphthylene.

The terms "ortho-branched phenylene", "meta-branched phenylene" and "para-branched phenylene" mean that the two lateral pyridines or pyridiniums (rings A and B) are branched on the central phenylene core (Z) in, respectively, the ortho position, the meta position or the para position as represented below (optional substituents on the central phenylene core are not shown):

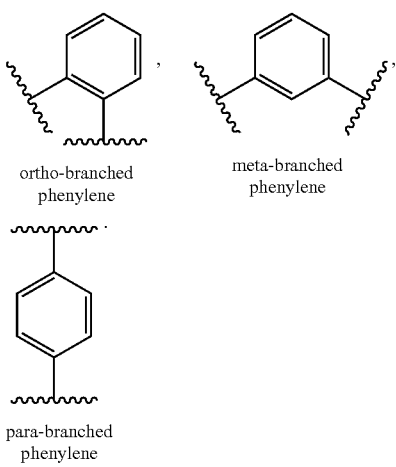

ortho-branched phenylene, meta-branched phenylene para-branched phenylene

The term "2,6-branched naphthylene" means that the two lateral pyridines or pyridiniums (rings A and B) are branched on the central naphthylene core (Z) in positions 2 and 6 as represented below (optional substituents on the central naphthylene core are not shown):

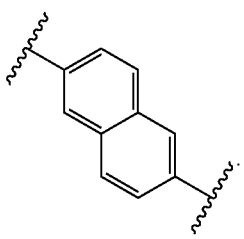 [SMILES: *c1ccc2cc(*)ccc2c1]

When Z is an ortho-branched phenylene, it is preferably an unsubstituted ortho-branched phenylene.

When Z is a meta-branched phenylene, it is preferably a substituted meta-branched phenylene. Preferably, said meta-branched phenylene is substituted by at least one N-alkylpyridinium group, more preferably substituted by two N-alkylpyridinium groups, even more preferably substituted by two N-hexylpyridinium groups.

When Z is a para-branched phenylene, it may be either unsubstituted or substituted. Preferably, said para-branched phenylene is unsubstituted or substituted with at least one halogen. More preferably, said para-branched phenylene is unsubstituted or substituted with at least one F atom. Even more preferably, said para-branched phenylene is unsubstituted or substituted with four F atoms.

When Z is a 2,6-branched naphthylene, it is preferably unsubstituted.

In a second embodiment of the present invention, the central core Z of the compound of formula (I) is a pyridinediyl radical. Said pyridinediyl radical may be selected from:
  2,3-branched pyridinediyl radical;
  2,4 branched pyridinediyl radical;
  2,5 branched pyridinediyl radical; or
  2,6 branched pyridinediyl radical.

Said pyridinediyl radical is preferably a 2,3 branched pyridinediyl radical, preferably unsubstituted.

The terms "2,3-branched pyridinediyl radical", "2,4-branched pyridinediyl radical", "2,5-branched pyridinediyl radical" and "2,6-branched pyridinediyl radical" mean that the two lateral pyridines or pyridiniums (rings A and B) are branched on the central core (Z) in, respectively, positions 2 and 3, positions 2 and 4, positions 2 and 5 or positions 2 and 6 as represented below (optional substituents or fused systems on the central core are not shown):

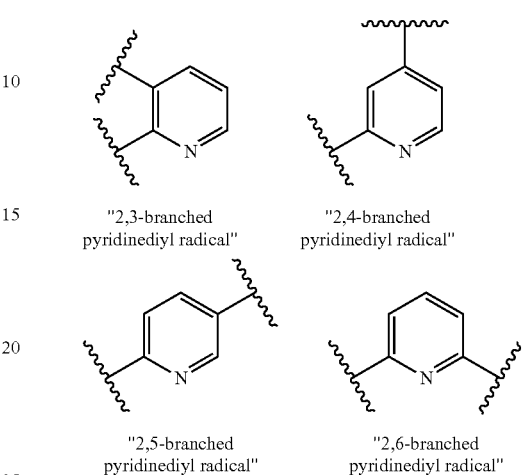

"2,3-branched pyridinediyl radical"    "2,4-branched pyridinediyl radical"

"2,5-branched pyridinediyl radical"    "2,6-branched pyridinediyl radical"

In a third embodiment of the present invention, the central core Z of the compound of formula (I) is a pyridiniumyl radical. Said pyridiniumyl radical may be selected from:
  1,2-branched pyridiniumyl radical;
  1,4-branched pyridiniumyl radical;
  2,3 branched pyridiniumyl radical;
  2,4 branched pyridiniumyl radical;
  2,5 branched pyridiniumyl radical;
  3,4 branched pyridiniumyl radical; or
  3,5 branched pyridiniumyl radical.

The terms "1,2-branched pyridiniumyl radical" and "1,4-branched pyridiniumyl radical" mean that the two lateral pyridines or pyridiniums (rings A and B) are branched on the central pyridinium core (Z) in, respectively, positions 1 and 2 or positions 1 and 4 as represented below (optional substituents or fused systems on the central pyridinium core are not shown):

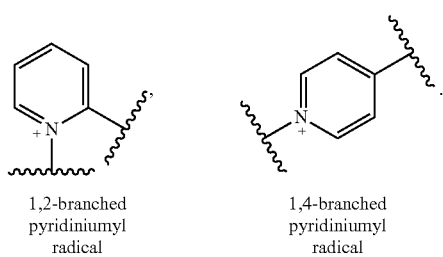

1,2-branched pyridiniumyl radical    1,4-branched pyridiniumyl radical

The terms "2,3-branched pyridiniumyl radical", "2,4-branched pyridiniumyl radical" and "2,5-branched pyridiniumyl radical" mean that the two lateral pyridines or pyridiniums (rings A and B) are branched on the central pyridinium core (Z) in, respectively, positions 2 and 3 or positions 2 and 4 or positions 2 and 5 as represented below (optional substituents or fused systems on the central pyridinium core are not shown):

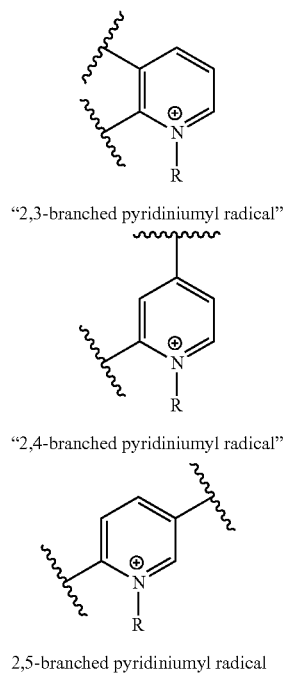

"2,3-branched pyridiniumyl radical"

"2,4-branched pyridiniumyl radical"

2,5-branched pyridiniumyl radical

The terms "3,4-branched pyridiniumyl radical" and "3,5 branched pyridiniumyl radical" mean that the two lateral pyridines or pyridiniums (rings A and B) are branched on the central pyridinium core (Z) in, respectively, positions 3 and 4 or positions 3 and 5 as represented below (optional substituents or fused systems on the central pyridinium core are not shown):

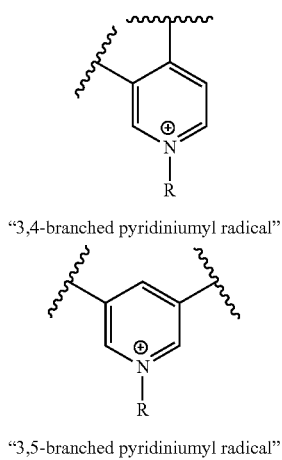

"3,4-branched pyridiniumyl radical"

"3,5-branched pyridiniumyl radical"

When Z is a 2,3-branched pyridiniumyl radical, 2,4-branched pyridiniumyl radical, 2,5-branched pyridiniumyl radical, 3,4-branched pyridiniumyl radical or 3,5-branched pyridiniumyl radical, the nitrogen of said pyridiniumyl radical is preferably substituted by an aryl or an alkyl, more preferably an alkyl and even more preferably an n-hexyl group (n-$C_6H_{13}$) or a methyl group.

According to this third embodiment of the present invention, said pyridiniumyl radical is preferably selected from:
1,2-branched pyridiniumyl radical;
1,4-branched pyridiniumyl radical;
3,4-branched pyridiniumyl radical; or
3,5 branched pyridiniumyl radical.

When Z is a 1,2-branched pyridiniumyl radical, it is preferably a substituted 1,2-branched pyridiniumyl radical. Preferably, said 1,2-branched pyridiniumyl radical is substituted by at least one aryl group, more preferably substituted by two aryl groups, even more preferably by two methylphenyl groups (—$C_6H_4CH_3$).

When Z is a 1,4-branched pyridiniumyl radical, it is preferably substituted or fused with at least one bicyclic system. Preferably, said 1,4-branched pyridiniumyl radical is substituted by at least one aryl group or fused with at least one 1,2,3,4-tetrahydronaphthalene system. More preferably, said 1,4-branched pyridiniumyl radical is substituted by two aryl groups or fused with two 1,2,3,4-tetrahydronaphthalene systems. Even more preferably, said 1,4-branched pyridiniumyl radical is substituted by two aryl groups selected from phenyl, methylphenyl (—$C_6H_4CH_3$), fluorophenyl (—$C_6H_4F$), or trifluoromethylphenyl ($C_6H_4CF_3$).

In a fourth embodiment of the present invention, the central core Z of the compound of formula (I) is as described above and each Y is N or ($^+$N—$R_9$)($X^-$) with $R_9$ a $C_3$-$C_{18}$ alkyl, a N-alkylpyridinium group or an aryl. Preferably, Y is N or ($^+$N—$R_9$)($X^-$) with $R_9$ a $C_6$-$C_8$ alkyl, a N—$C_3$-$C_{18}$ alkylpyridinium or a phenyl. More preferably, Y is ($^+$N—$R_9$)($X^-$) with $R_9$ an unsubstituted $C_6$-$C_7$ alkyl, a N—$C_5$-$C_7$ alkylpyridinium or a substituted phenyl. Even more preferably, Y is ($^+$N—$R_9$)($X^-$) with $R_9$ n-hexyl (n-$C_6H_{13}$), a N-hexylpyridinium or a phenyl substituted with at least one methyl group or one isopropyl group.

When Y is N, n is preferably equal to 1.

When Y is ($^+$N—$R_9$)($X^-$) with $R_9$ as defined above, n is preferably equal to 2, 3 or 4.

In a fifth embodiment of the present invention, Z and Y are as defined above and each one of $R_1$-$R_8$ is independently selected from H, alkyl, alkoxy, alkylthio, haloalkyl, haloalkoxy, haloalkylthio, polyalkylenoxy, alkoxycarbonyl, aryl or heteroaryl. Preferably, each one of $R_1$-$R_8$ is H.

The counterion $X^-$ may be any anion that maintains electric neutrality of the compounds of formula (I). $X^-$ may be selected from halide, preferably fluoride and chloride, tetrafluoroborate, tetraphenylborate, hexafluorophosphate, nitrate, methanesulfonate, trifluoromethanesulfonate, toluenesulfonate, hexachloroantimonate, bis(trifluoromethanesulfonyl)imide, perchlorate, acetate and sulfate. Preferably, $X^-$ is tetrafluoroborate.

Electrochromic compounds according to the invention are preferably well soluble in solvent medium. Hence, electrochromic compounds preferably do not contain functional groups limiting solubility. In particular electrochromic compounds preferably do not contain a sulfonate group, a phosphonate group, a phosphate group, a phosphoric acid group, a trichlorosilyl group, a trialkoxysilyl group, a monochlorosilyl group, and a monoalkoxysilyl group.

In a particularly preferred embodiment of the present invention, the compound of formula (I) is selected from the group consisting of:

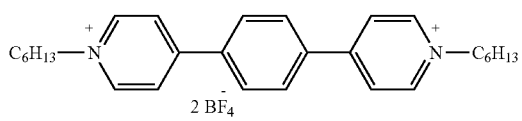

-continued
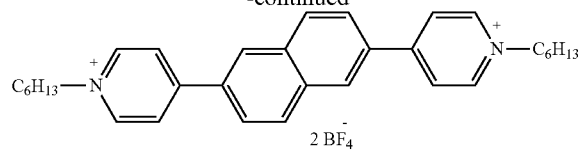
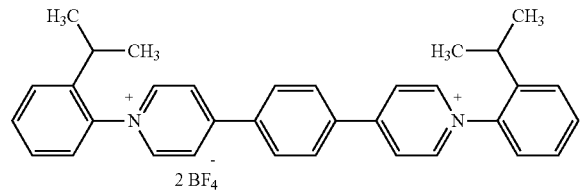
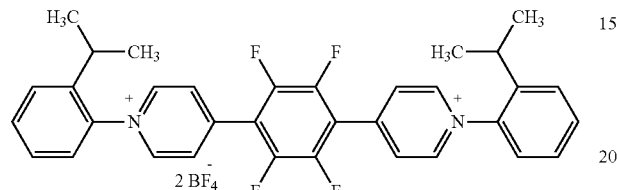
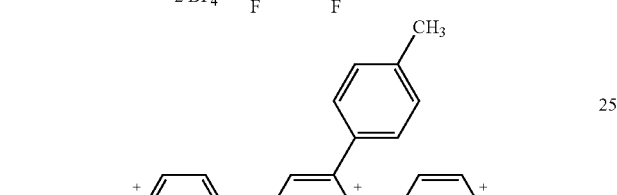
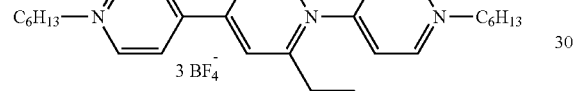
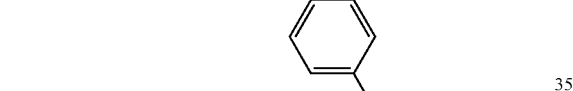
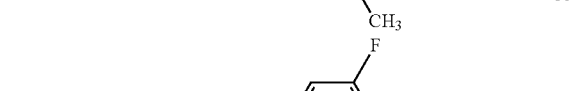
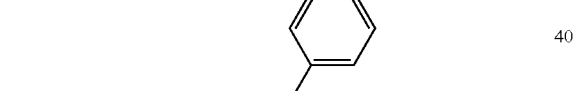
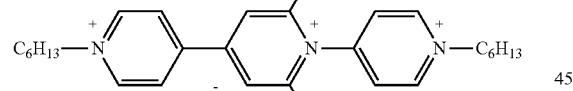
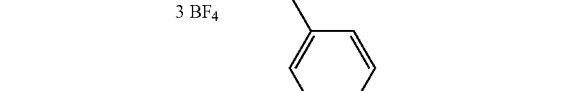
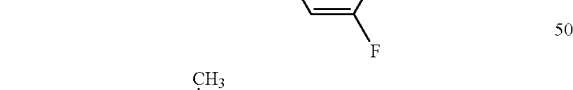
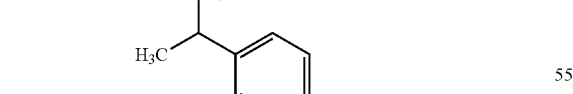
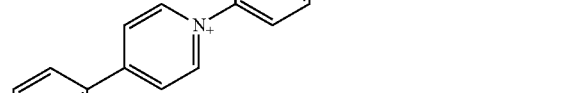
-continued
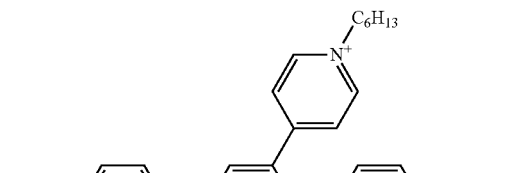
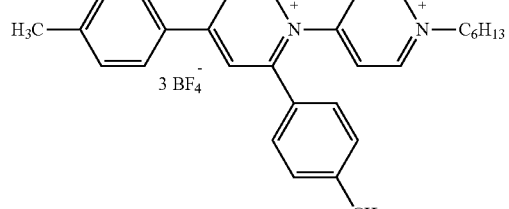
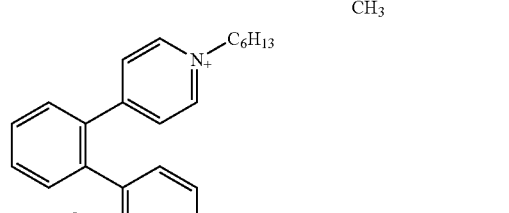
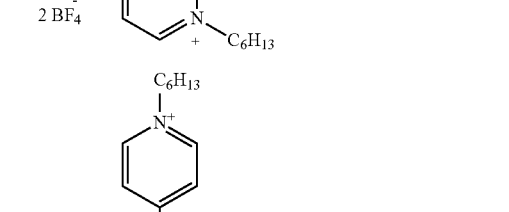
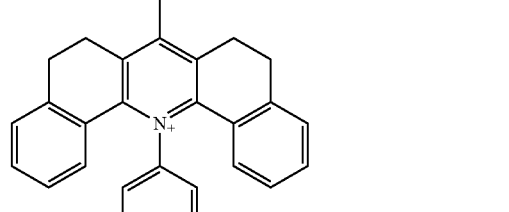
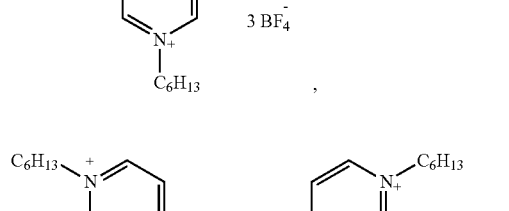
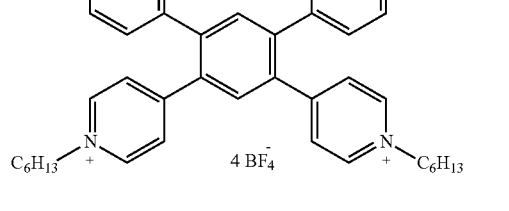
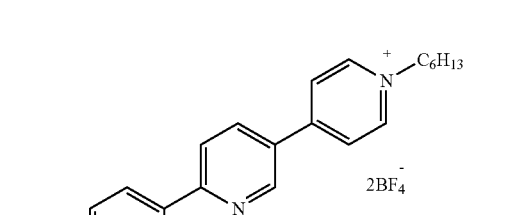

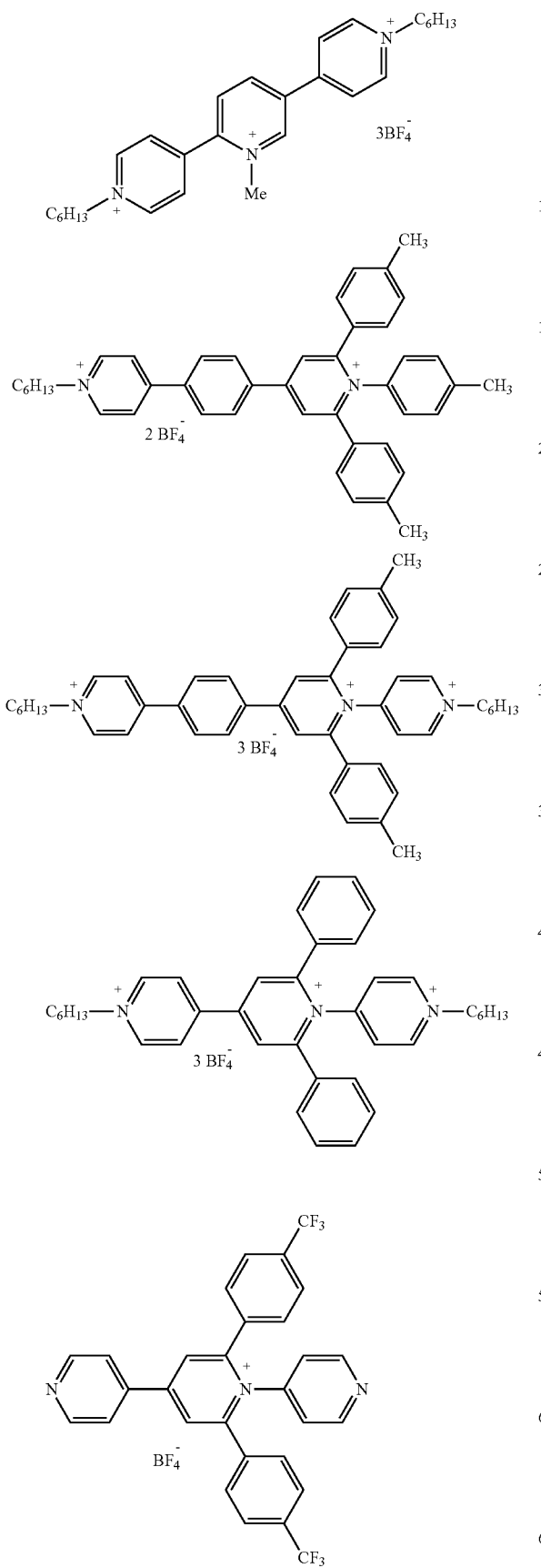
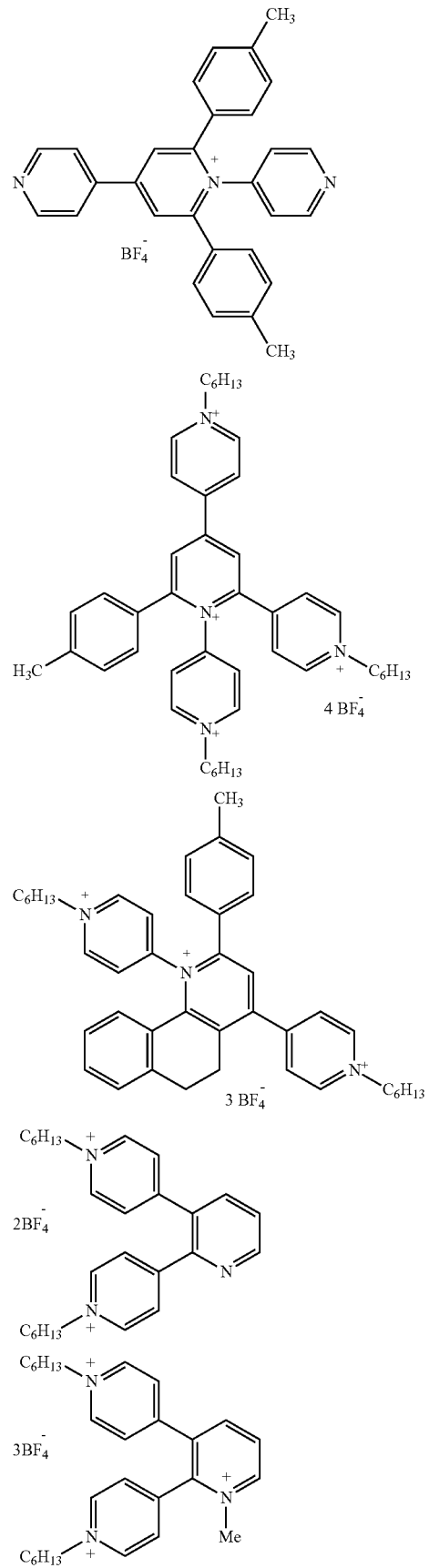

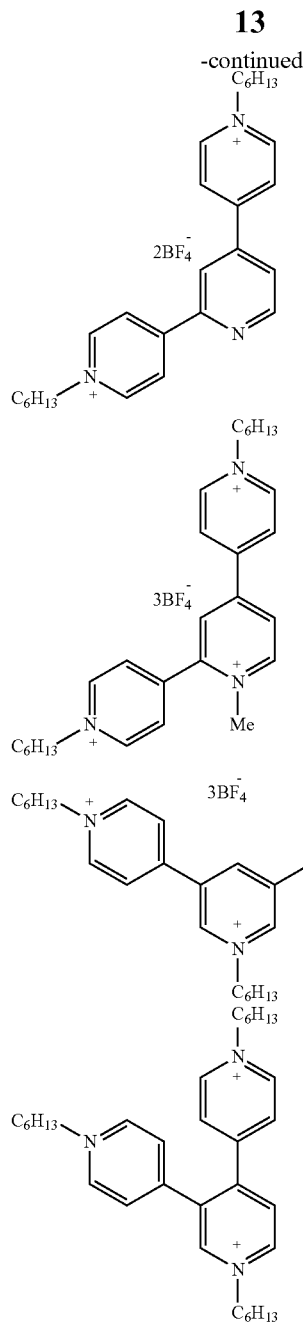

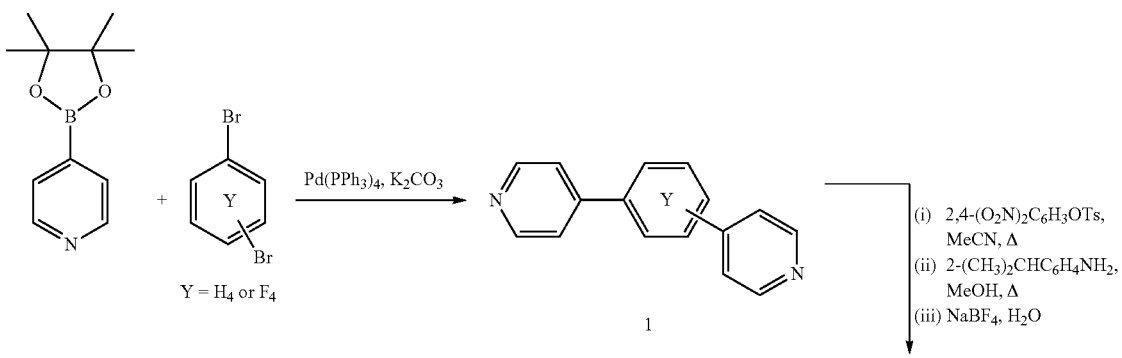

Compounds represented by formula (I) may be prepared according to various methods well known in the art.

For example, compounds having a $C_6$-$C_{10}$ arylene central core may be obtained according to the synthetic route detailed hereinafter Suzuki-Miyaura coupling of 4-(4,4,5,5-tetramethyl-1,3,2-dioxoborolan-2-yl)pyridine (V. Diemer, H. Chaumeil, A. Defoin, P. Jacques and C. Carre, *Tetrahedron Lett.*, 2005, 46, 4737) with the appropriate dibromobenzene derivative proceeds smoothly to generate the corresponding bis(4-pyridyl) benzene intermediates 1 (Scheme 1). All the isomers are known compounds (Y.-S. Su and C.-F. Chen, *Org. Lett.*, 2010, 12, 1888; M. Fujita, H. Oka and K. Ogura, *Teterahedron Lett.*, 1995, 36, 5247). Subsequent alkylation with the appropriate iodoalkane can be accomplished by heating in an appropriate solvent, such as acetonitrile. Following completion of the reaction, counter-ion exchange of the bis(pyridinium) salt can be effected by treatment with aqueous sodium tetrafluoroborate. N-Arylation of intermediates 1 can be accomplished using the well-established Zincke methodology (W.-C. Cheng and M. J. Kuth, *Org. Prep. Proced. Int.*, 2002, 34, 585) involving initial formation of the bis(N-2,4-dinitrophenyl) derivative via an $S_NAr$ reaction with 2,4-dinitrophenyl p-toluenesulfonate in acetonitrile. Subsequent reaction of the Zincke salt with an aromatic amine followed by anion exchange in the usual manner gives the ring-separated viologens of formula 2.

An analogous procedure can be applied to 1,2,4,5-tetrabromobenzene to afford the tetrakis(pyridinium) salts of formula 3.

That the arylene core is not limited to a phenylene spacer is illustrated by the Suzuki-Miyaura coupling of 4-(4,4,5,5-tetramethyl-1,3,2-dioxoborolan-2-yl)pyridine with naphthalene-2,6-diyl bis(trifluoromethanesulfonate) (M. Takeuchi, T. Tuihiji and J. Nishimura, *J. Org. Chem.*, 1993, 58 7388) to afford 2,6-bis(4-pyridyl)naphthalene (M.-J. Lin, A. Jouaiti, N. Kyritsakas and M. W. Hosseini, *CrystEngComm*, 2011, 3, 776). The latter can be readily alkylated under standard conditions (Scheme 1).

Scheme 1

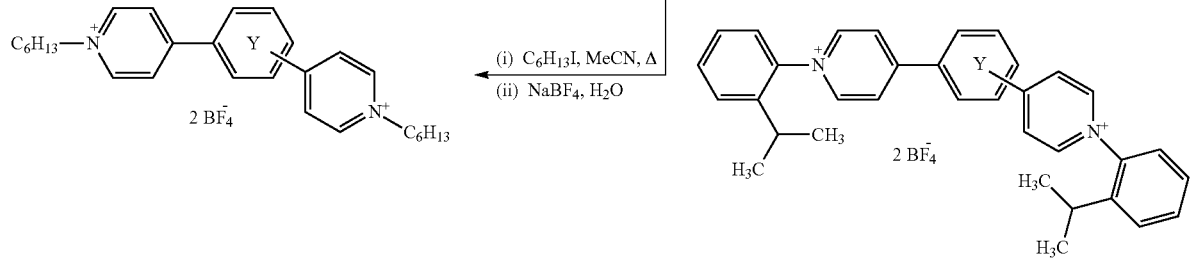

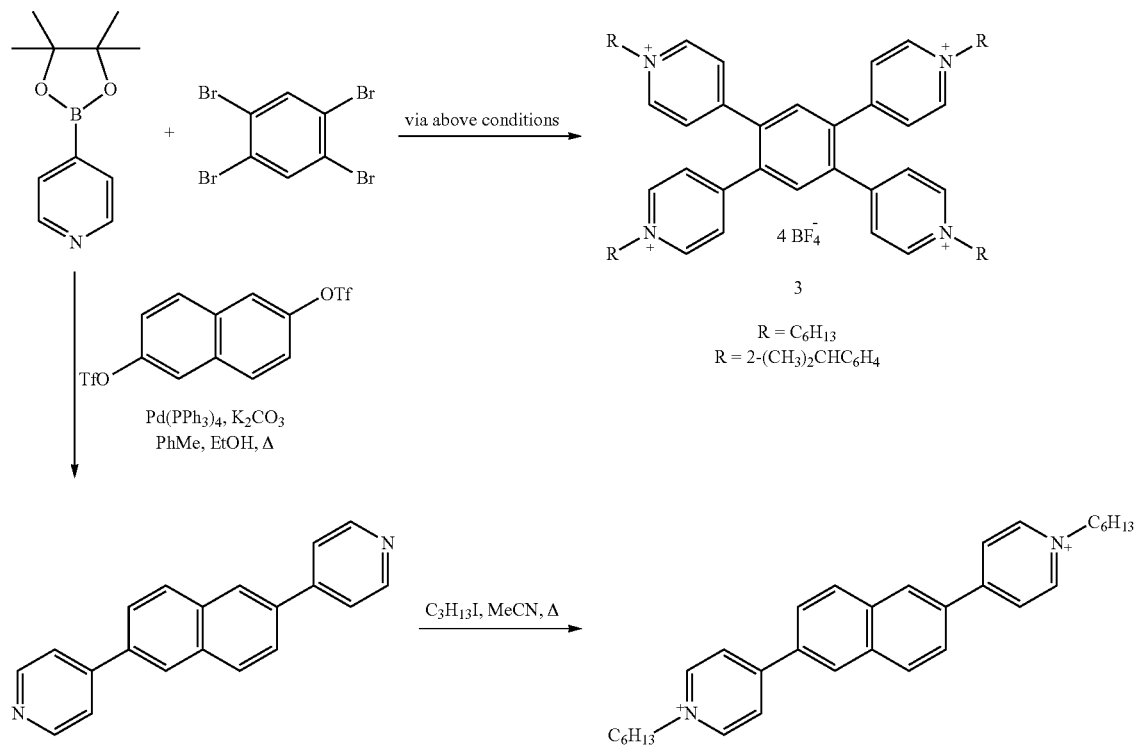

Compounds having a pyridinium radical central core may be obtained by reacting the key intermediates, the pyrylogens 4 with 4-aminopyridine according to the synthetic route detailed in scheme 2. The pyrylogens 4 may be obtained by standard literature procedures that are known to those in the field (E. L. Clennan, C. Liao and E. Ayokosk, *J. Am. Chem. Soc.*, 2008, 130, 7552). An extension of this procedure has been employed to synthesise ring-separated bi- and tri-pyridiniums via the pyrylogen 5. For these examples readily available 4-(4-pyridyl)benzaldehyde (R. Mueller, M. Huerzeler and C. Boss, *Molecules*, 2003, 8, 556) serves as a convenient starting material (Scheme 2).

Scheme 2

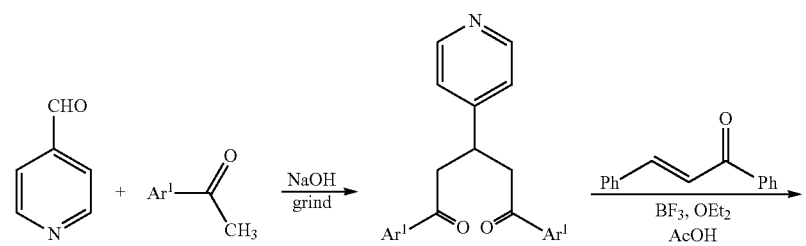

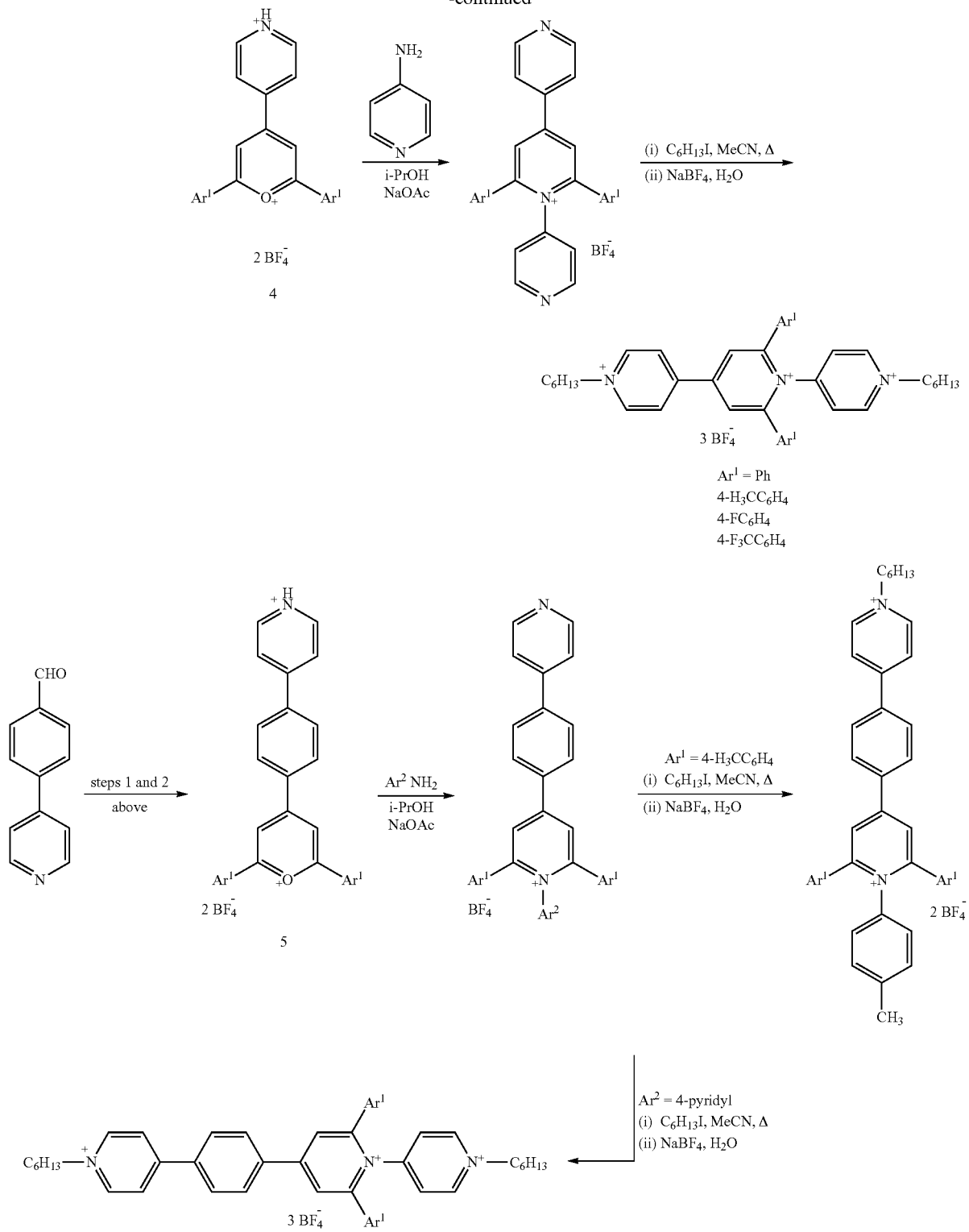

A related approach can be employed to synthesise compounds containing the 4,1′:2′,4″-terpyridine-1,1′,1″-triium core as shown in scheme 3 and is based upon a variation of literature procedures (J. E. Downes, *J. Chem. Soc.* (C), 1967, 1491; S. Aiken, D. L. Crossley, C. D. Gabbutt, B. M. Heron, C. Biver, S. Archambeau and F. Berit-Debat, EP 2848668A1). Heterologues containing an additional pyridinium subsitituent can also be prepared by this approach via based-mediated conjugate addition of 4-acetylpyridine to trans-3-(4-pyridyl)-1-(p-tolyl)prop-2-en-1-one (R. Bauer, P. Nussbaumer and M. Neumann-Spallart, *Z. Naturforsch. B,* 1988, 43, 475). This variation is also shown in scheme 3.

Scheme 3

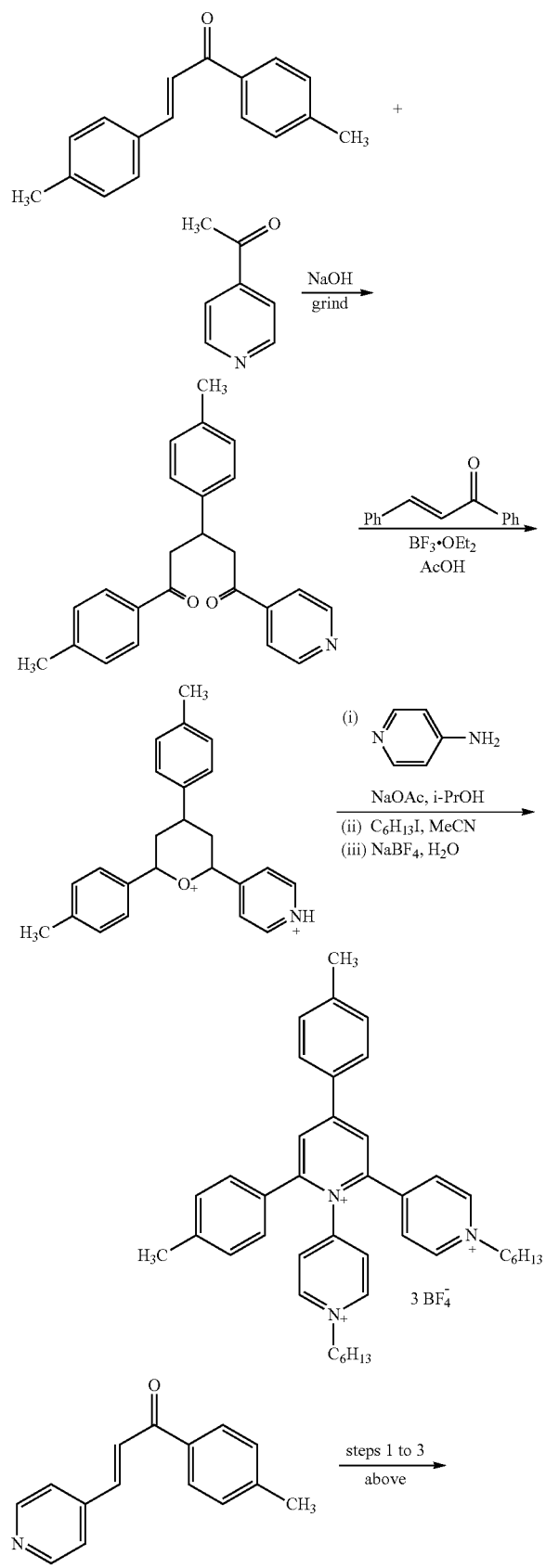

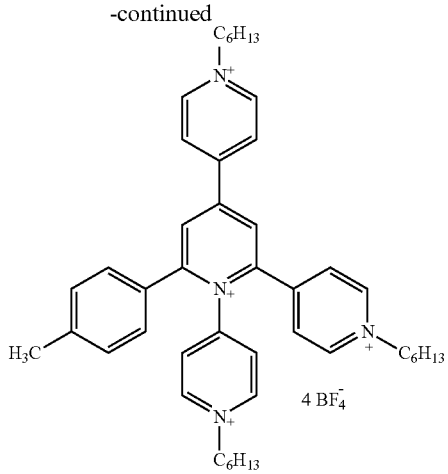

Compounds of the type depicted in Scheme 2 in which the C-2 and/or C-6 aryl substituents in the central pyridinium ring are conjoined with the C-3 and C-5 positions to form 1,2,3,4-tetrahydronaphthalene rings can be synthesised from 1-tetralone by the procedures outlined in schemes 4 and 5.

The mono-annulated pyrylogen 6 can be obtained via base-mediated conjugate addition of trans-3-(4-pyridyl)-1-(p-tolyl)prop-2-en-1-one to 1-tetralone and then converted to the terpyridintrium salt (Scheme 4).

Scheme 4

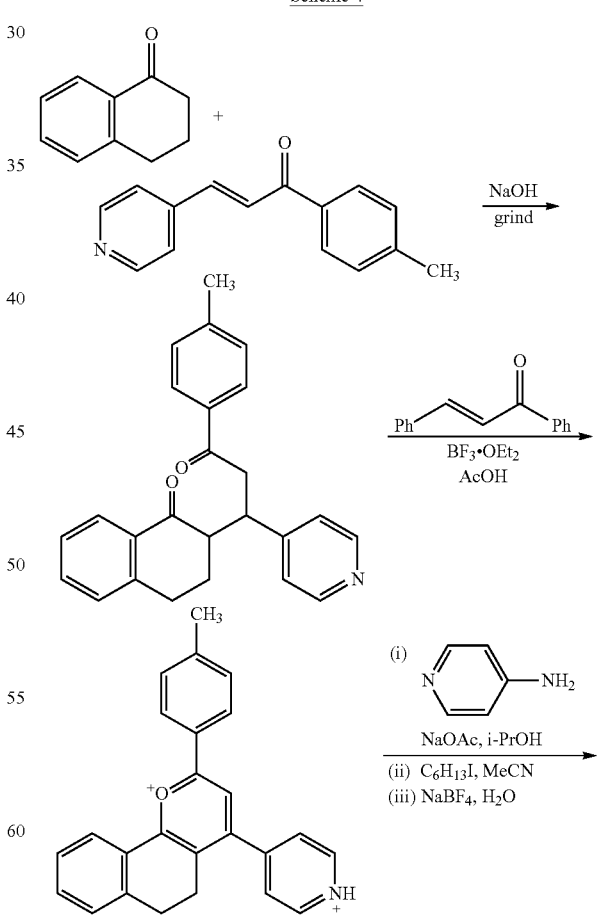

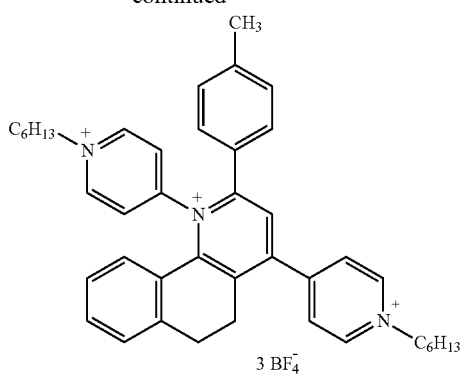

A doubly-annulated terpyridinium system can be obtained via the xanthylium salt 7 (Scheme 5)

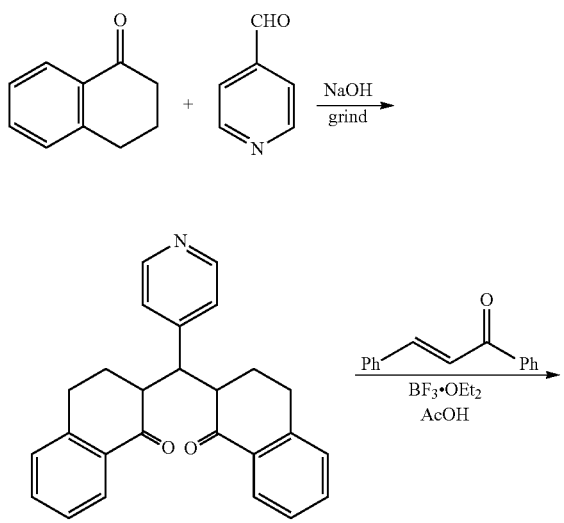

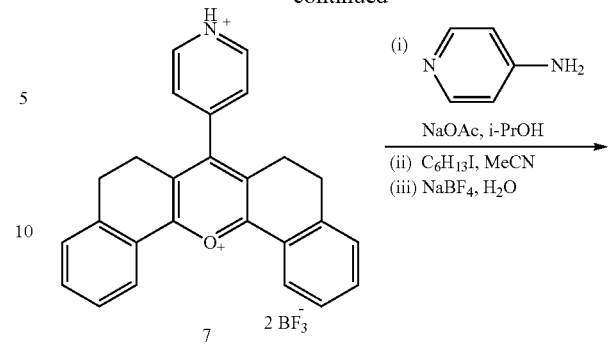

In a similar manner to the route outlined in scheme 1, the six isomeric dibromopyridines can be subjected to Suzuki-Miyuara coupling with 4-(4,4,5,5-tetramethyl-1,3,2-dioxoborolan-2-yl)pyridine, to generate the corresponding terpyridines. Two of the isomers can be quaternised directly with 1-iodohexane. The remaining four isomers are quaternised on the terminal pyridyl substituents. For three compounds the central pyridine core is alkylated by treatment with trimethyloxonium tetrafluoroborate (Scheme 6).

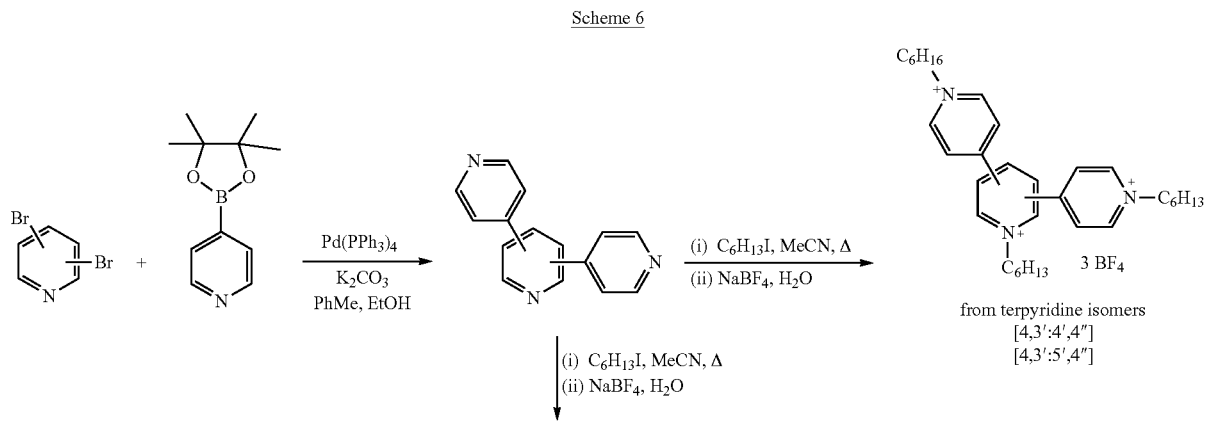

-continued

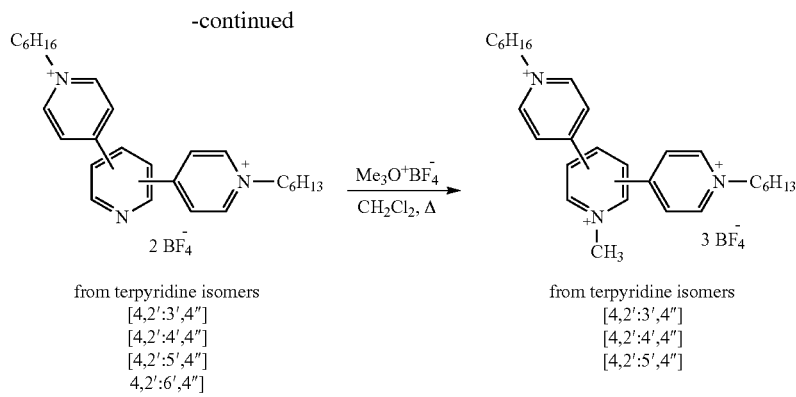

from terpyridine isomers
[4,2':3',4"]
[4,2':4',4"]
[4,2':5',4"]
4,2':6',4"]

from terpyridine isomers
[4,2':3',4"]
[4,2':4',4"]
[4,2':5',4"]

Electrochromic Composition

The present invention also relates to electrochromic compositions comprising at least one compound of formula (I) as defined above as an oxidizing electrochromic compound. One or more additional oxidizing electrochromic compounds can be added to the composition of the invention so as to adapt the colour or the intensity of the coloured state of the composition. Said additional compound can be another compound of formula (I) or a different compound such as compatible dyes or pigments. For example, the additional oxidizing electrochromic compound can be selected from alkylviologens, arylviologens, alkylarylviologens or anthraquinone and derivatives. Preferably, the additional compound has a redox potential close to the compound of formula (I).

The composition may also comprise at least one reducing compound. The reducing compound may also be an electrochromic compound. Example of reducing compounds include 5,10-dihydrophenazine, phenothiazine, phenoxazine, N,N,N',N'-tetramethyl-p-phenylenediamine, thioanthrene, tetrathiafulvalene, ferrocene and their derivatives.

The composition of the invention may comprise a host medium that may be a fluid, a mesomorphous medium or a gel. The host medium is introduced in the composition of the invention to dissolve the electrochromic compounds so as to form a solution of the electrochromic compounds. The host medium is preferably selected from the group consisting of organic solvents, liquid crystals, polymers, liquid crystal polymers and mixtures thereof.

Electrochromic compounds according to the invention are preferably well soluble in solvent medium. Hence, electrochromic compounds preferably do not contain functional groups limiting solubility. In particular electrochromic compounds preferably do not contain a sulfonate group, a phosphonate group, a phosphate group, a phosphoric acid group, a trichlorosilyl group, a trialkoxysilyl group, a monochlorosilyl group, and a monoalkoxysilyl group.

Examples of suitable organic solvents that can be used as host medium are redox-compatible solvents which cannot react with the electrochromic compounds of the composition, such as ethylene carbonate, propylene carbonate, γ-butyrolactone, γ-valerolactone, acetonitrile, propionitrile, benzonitrile, glutaronitrile, methylglutaronitrile, dimethylformamide, N-methylpyrrolidone, sulfolane, 3-methyl sulfolane, benzene, toluene, methyl ethyl ketone, acetone, ethanol, tetrahydrofurfuryl alcohol, 2-methoxyethyl ether, xylene, cyclohexane, 3-methylcyclohexanone, ethyl acetate, ethyl phenylacetate, tetrahydrofuran, methanol, methyl propionate, ethylene glycol, ethylene carbonate, ionic liquids, and mixtures thereof. Preference is given to carbonates and particularly propylene carbonate.

Examples of suitable liquid crystals that can be used as host medium are nematic or chiral nematic media.

Examples of suitable polymers that can be used as host medium are polymers which are soluble with the solvent, in particular PMMA or other acrylate polymers, polyurethane, polyethylene oxide, polypropylene oxide, polyvinyl acetate, poly(N-vinyl pyrrolidone), and polyvinylidene fluoride.

Examples of suitable liquid crystal polymers that may be used as host medium are Merck RM257 (Merck), LC242 (BASF) or SLM 90519 (Wacker). These liquid crystal polymers are generally used in combination with an organic solvent, for example one of the organic solvents mentioned above.

Electrochromic Device

The present invention also relates to an electrochromic device comprising a compound of formula (I) or a composition according to the invention. Said device may be selected from an optical article, preferably an optical lens, or an optical filter, a window, preferably an aircraft window, a visor, a mirror and a display, in particular a segmented or matrix display. Preferably, the device of the invention is an optical article, more preferably an optical lens, and even more preferably an ophthalmic lens.

Non-limiting examples of ophthalmic lens include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive, marine and aircraft windows, filters, shutters, and optical switches.

Preferably, the device of the invention comprises a mechanism for holding the compound or composition of the invention in a mechanically stable environment. More preferably, said device may comprise a pair of opposed substrates having a gap there between for receiving the mixture of the host medium and said compound or said composition of the present invention, and a frame for holding said pair of substrates adjacent one another.

The device of the present invention may thus comprise an optical component provided with at least one transparent cell arrangement juxtaposed in a parallel direction to the surface thereof, as disclosed in WO 2006/013250, each cell being tightly closed and containing at least one compound or composition of the present invention.

Other devices according to the invention can be devices as described in FR 2937154 or FR2950710 comprising at least one compound or composition of the invention.

EXAMPLES

This invention will be further illustrated by the following non-limiting examples which are given for illustrative purposes only and should not restrict the scope of the appended claims.

Example 1: Synthesis of 4,4'-(1,4-phenylene)bis(1-hexylpyridin-1-ium) bis(tetrafluroborate)

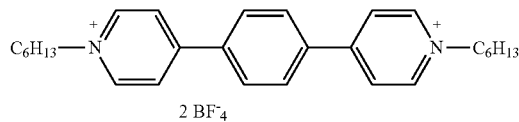

A mixture of 4-(4,4,5,5-tetramethyl-1,3,2-dioxaborolan-2-yl)pyridine (4.34 g, 21.2 mmol), 1,4-dibromobenzene (2.00 g, 8.5 mmol), $K_2CO_3$ (2.92 g, 21.2 mmol) and $Pd(PPh_3)_4$ (0.49 g, 5 mol %) in PhMe (30 mL) and EtOH (30 mL) under $N_2$ was heated at reflux for 48 h. The resulting mixture was poured into water (50 mL), extracted with dichloromethane (2×100 mL), dried ($MgSO_4$) and the solvent removed under reduced pressure. The residue was chromatographed on silica using MeOH (0-5%) in dichloromethane as eluent. The solvent was removed under reduced pressure and the residue crystallised from hot EtOAc/hexanes to give 1,4-di(4-pyridyl)benzene (1.52 g, 77%) as a pale yellow powder. A mixture of 1,4-di(4-pyridyl)benzene (0.82 g, 3.5 mmol) and 1-iodohexane (3.75 g, 17.7 mmol) in MeCN (30 mL) was heated under reflux in the dark for 16 h, cooled, filtered and washed with MeCN to give 4,4'-(1,4-phenylene)bis(1-hexylpyridin-1-ium) diiodide (1.10 g, 47%) as a brown powder.

A solution of 4,4'-(1,4-phenylene)bis(1-hexylpyridin-1-ium) diiodide (0.55 g, 0.8 mmol) in MeOH (15 mL) was added dropwise to a solution of $NaBF_4$ (1.11 g, 10.1 mmol) in water (50 mL) with stirring. The resulting mixture stirred for 0.5 h, filtered, washed with water (2×5 mL) and air dried to give 4,4'-(1,4-phenylene)bis(1-hexylpyridin-1-ium) bis (tetrafluroborate) (0.43 g, 90%) as a pale yellow powder. $\delta_H$ (400 MHz $CD_3OD$) 9.06 (4H, d, J=6.8 Hz), 8.53 (4H, d, J=6.8 Hz), 8.29 (s, 4H), 4.67 (4H, t, J=7.6 Hz), 2.30-2.05 (m, 4H), 1.55-1.30 (m, 12H) and 0.96 (6H, t, J=7.6 Hz). $\delta_F$ (376 MHz $CD_3OD$) −154.4-−154.6.

Example 2: Synthesis of 4'-(naphthalene-2,6-diyl) bis(1-hexylpyridin-1-ium) bis(tetrafluoroborate)

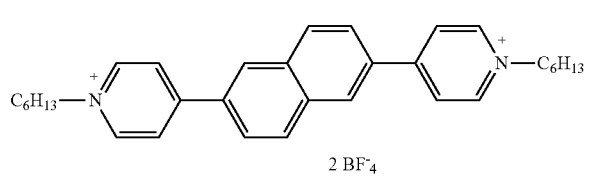

A solution of trifluoromethansulfonic anhydride (9.7 g, 34.3 mmol) in DCM (80 mL) was added dropwise at 0° C. with stirring to a solution of 2,6-dihydroxynaphthalene (2.5 g, 15.6 mmol) and pyridine (2.99 g, 37.8 mmol) in dichloromethane (80 mL) at 0° C. under $N_2$. Stirring was continued for 1 h and the resulting mixture poured into water (200 mL), separated, the organic phase dried ($MgSO_4$) and the solvent removed under reduced pressure. The residue was filtered through a short plug of silica using dichloromethane (80% in hexanes) as eluent. The solvent was removed under reduced pressure and the residue crystallised from hot hexanes containing a few drops of dichloromethane to give naphthalene-2,6-diyl bis(trifluoromethanesulfonate) (5.67 g, 86%) as pale pink prisms. A mixture of 4-(4,4,5,5-tetramethyl-1,3,2-dioxaborolan-2-yl)pyridine (4.83 g, 23.6 mmol), naphthalene-2,6-diyl bis(trifluoromethanesulfonate) (4 g, 9.4 mmol), $K_2CO_3$ (3.26 g, 23.6 mmol) and $Pd(PPh_3)_4$ (0.54 mg, 5 mol %) in PhMe (40 mL) and EtOH (40 mL) under $N_2$ was heated at reflux for 72 h. The resulting mixture was poured into water (100 mL), extracted with EtOAc (4×100 mL), dried ($MgSO_4$) and the solvent removed under reduced pressure. The residue was chromatographed on silica using MeOH (0-10% in EtOAc) as eluent. The first band was collected and the solvent removed under reduced pressure. The residue was triturated with EtOAc/pet. ether (40-60) to give 6-(4-pyridyl)-2-naphthol (0.44 g, 21%) as a yellow powder. The second band was collected and the solvent removed under reduced pressure and the residue rechromatographed using MeOH (0-10% in EtOAc) as eluent. The second band was again collected and the solvent removed under reduced pressure. The residue was triturated with EtOAc/pet. ether (40-60) to give 2,6-di(4-pyridyl)naphthalene (0.98 g, 37%) as a pale yellow powder.

A mixture of 2,6-di(4-pyridyl)naphthalene (0.60 g, 2.1 mmol) and 1-iodohexane (2.25 g, 10.6 mmol) in MeCN (30 mL) was heated under reflux in the dark for 16 h, cooled, filtered and washed with $Et_2O$ (10 mL) to give 4,4'-(naphthalene-2,6-diyl)bis(1-hexylpyridin-1-ium) diiodide (1.44 g, 96%) as a yellow powder.

A solution of 4,4'-(naphthalene-2,6-diyl)bis(1-hexylpyridin-1-ium) diiodide (0.5 g, 0.7 mmol) in MeOH (60 mL) was added dropwise to a solution of $NaBF_4$ (1.41 g, 12.8 mmol) in water (100 mL) with stirring. The resulting mixture was heated to dissolution then reduced in volume and the resulting precipitate filtered, washed with water (2×10 mL) and air dried to give 4,4'-(naphthalene-2,6-diyl)bis(1-hexylpyridin-1-ium) bis(tetrafluoroborate) (0.42 g, 95%) as a bright yellow powder.

$\delta_H$ (400 MHz $CD_3OD$) 9.01 (4H, d, J=7.2 Hz), 8.74 (2H, d, J=1.6 Hz), 8.59 (4H, d, J=7.2 Hz), 8.39 (2H, d, J=8.4 Hz), 8.21 (2H, dd, J=1.6 and 8.4 Hz), 4.68 (4H, t, J=7.6 Hz), 2.20-2.00 (m, 4H), 1.50-1.30 (m, 12H) and 0.93 (6H, t, J=7.6 Hz).

$\delta_F$ (376 MHz $CD_3OD$-$D_2O$) −152.84-−152.96.

Example 3: Synthesis of 4,4'-(1,4-phenylene)bis[1-(2-isopropylphenyl)pyridin-1-ium] bis(tetrafluoroborate)

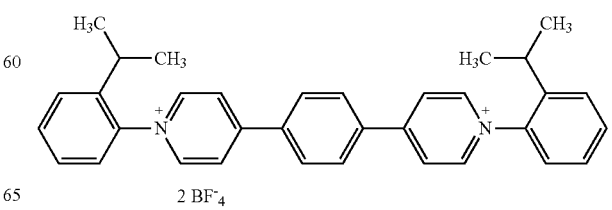

A solution of 1,4-di(4-pyridyl)benzene (1.00 g, 4.3 mmol) and 2,4-dinitrophenyl p-toluenesulfonate (3.20 g, 13.8 mmol) in MeCN (40 mL) was heated at reflux. After 16 h additional 2,4-dinitrophenyl p-toluenesulfonate (0.50 g) was added and reflux continued for 8 h more. The resulting precipitate was cooled, filtered, washed with cold MeCN (30 mL) and air dried to give 4,4'-(1,4-phenylene)bis[1-(2,4-dinitrophenyl)pyridin-1-ium] bis(p-toluenesulfonate) (3.71 g, 95%) as a pale yellow powder.

A suspension of 4,4'-(1,4-phenylene)bis[1-(2,4-dinitrophenyl)pyridin-1-ium] bis(p-toluenesulfonate) (3.50 g, 3.85 mmol) and NaBF$_4$ (2.54 g, 23 mmol) in MeOH (150 mL) and water (100 mL) was stirred at rt for 2 h then filtered. The filtrand and NaBF$_4$ (2.54 g, 23 mmol) was suspended in MeOH (150 mL) and water (100 mL) and stirred for 2 h, filtered, washed with water (3×50 mL) and air dried to give the 4,4'-(1,4-phenylene)bis[1-(2,4-dinitrophenyl)pyridin-1-ium] bis(tetrafluoroborate) (2.81 g, 95%) as a pale yellow powder.

A mixture of 4,4'-(1,4-phenylene)bis[1-(2,4-dinitrophenyl)pyridin-1-ium] bis(tetrafluoroborate) (1.40 g, 1.9 mmol) and 2-isopropylaniline (1.53 g, 11.3 mmol) in MeOH (30 mL) was heated at reflux for 24 h, cooled and the solvent removed under reduced pressure. The residue was thrice triturated with hot EtOH, and the extracts were then cooled and filtered. The residue was dissolved in hot EtOH containing a few drops of water, filtered, cooled to 0° C., filtered, washed with cold EtOH (5 mL) and air dried to give the 4,4'-(1,4-phenylene)bis[1-(2-isopropylphenyl)pyridin-1-ium] bis(tetrafluoroborate) (0.56 g, 46%) as a cream powder.

$\delta_H$ (400 MHz DMSO-d$_6$) 9.41 (4H, d, J=6.8 Hz), 8.87 (4H, d, J=6.8 Hz), 8.54 (4H, s), 7.80-7.66 (m, 6H), 7.62-7.52 (m, 2H), 2.54-2.44 (m 2H partially obscured by DMSO signal) and 1.22 (6H, d, J=6.4 Hz).

$\delta_F$ (376 MHz DMSO-d$_6$) −148.07--148.34.

Example 4: Synthesis of 4,4'-(perfluoro-1,4-phenylene)bis(1-(2-isopropylphenyl)pyridin-1-ium) bis(tetrafluoroborate)

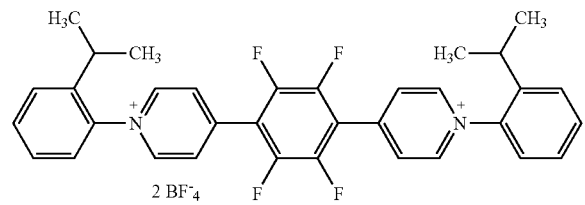

A mixture of 4-(4,4,5,5-tetramethyl-1,3,2-dioxaborolan-2-yl)pyridine (7.54 g, 36.8 mmol), 1,4-dibromo-2,3,5,6-tetrafluorobenzene (5.15 g, 16.7 mmol), K$_2$CO$_3$ (5.07 g, 36.8 mmol) and Pd(PPh$_3$)$_4$ (0.96 g, 5 mol %) in PhMe (50 mL) and EtOH (50 mL) under N$_2$ was heated at reflux for 48 h. The resulting mixture was poured into water (200 mL), extracted with dichloromethane (8×300 mL), dried (Na$_2$SO$_4$) and the solvent removed under reduced pressure. The residue was twice triturated with PhMe/hexanes, washed with hexanes and air dried to give the 4,4'-(perfluoro-1,4-phenylene)dipyridine (3.70 g, 73%) as a tan powder.

A solution of 4,4'-(perfluoro-1,4-phenylene)dipyridine (1.50 g, 4.9 mmol) and 2,4-dinitrophenyl p-toluenesulfonate (5.00 g, 14.8 mmol) in MeCN (40 mL) was heated at reflux. After 16 h additional 2,4-dinitrophenyl p-toluenesulfonate (1.50 g) was added and reflux was continued for 24 h more. The resulting precipitate was cooled, filtered, washed with cold MeCN (30 mL) and air dried to give (3.82 g) as a pale yellow powder. A suspension of the crude solid (3.63 g, 3.7 mmol) and NaBF$_4$ (2.45 g, 22.3 mmol) in MeOH (50 mL) and water (50 mL) was heated at reflux for 1 h, filtered hot, washed with water (2×10 mL) and air dried to give the 4,4'-(perfluoro-1,4-phenylene)bis(1-(2,4-dinitrophenyl)pyridin-1-ium) bis(tetrafluoroborate) (3.00 g, 100%) as a cream powder. A mixture of 4,4'-(perfluoro-1,4-phenylene)bis[1-(2,4-dinitrophenyl)pyridin-1-ium] tetrafluoroborate (1.50 g, 1.53 mmol) and 2-isopropylaniline (1.24 g, 9.2 mmol) in MeOH/water (6/1, 35 mL) was heated at reflux for 4 h, cooled and the solvent removed under reduced pressure. The residue was twice triturated with hot MeOH (10 mL), cooled, filtered and air dried to give the 4,4'-(perfluoro-1,4-phenylene)bis(1-(2-isopropylphenyl)pyridin-1-ium) bis(tetrafluoroborate) (0.89 g, 81%) as a cream powder.

$\delta_H$ (400 MHz DMSO-d$_6$) 9.53 (4H, d, J=6 Hz), 8.70 (4H, d, J=6 Hz), 7.83-7.72 (m, 6H), 7.64-7.53 (m, 2H), 2.59-2.49 (m 2H partially obscured by DMSO signal) and 1.230 (6H, d, J=6.4 Hz).

$\delta_F$ (376 MHz DMSO-d$_6$) −148.13--148.42.

Example 5: Synthesis of 1,1'''-dihexyl-2',6'-di-p-tolyl-[4,1':4',4''-terpyridine]-1,1',1'''-triium tris(tetrafluoroborate)

A solution of 4-(2,6-di-p-tolylpyrylium-4-yl)pyridin-1-ium bis(tetrafluoroborate) (A. Kanitz, M. Maleika, W. Roth D E 10 2012 201 673) (4.00 g, 7.8 mmol), 4-aminopyridine (0.88 g, 9.3 mmol), NaOAc (2.56 g, 31.2 mmol) in propan-2-ol (60 mL) was heated at reflux for 16 h, cooled and water (100 mL) was added. The solvent was removed and MeOH (100 mL) was added. The resulting solution was diluted with water (4 L), the solvent reduced in volume and the sticky precipitate was filtered through celite. The solvent was removed under reduced pressure and the residue dissolved in MeOH (10 mL) and added dropwise to water (70 mL) with rapid stirring. Stirring was continued for 0.5 h and the resulting precipitate was filtered and air dried to give 2',6'-di-p-tolyl-[4,1':4',4''-terpyridin]-1'-ium tetrafluoroborate (2.67 g, 68%) as yellow powder.

A solution of 2',6'-di-p-tolyl-[4,1':4',4''-terpyridin]-1'-ium tetrafluoroborate (0.75 g, 1.5 mmol) and 1-iodohexane (6.30 g, 31 mmol) in MeCN (20 mL) was heated at reflux for 2 days, cooled, the solvent reduced and Et$_2$O was added. The resulting precipitate was dissolved in a minimum MeCN and Et₂O added. The precipitate was filtered, washed with Et₂O and air dried to give 1,1"-dihexyl-2',6'-di-p-tolyl-[4,1':4',4"-terpyridine]-1,1',1"-triium tetrafluoroborate diiodide (1.08 g, 78%) as brown powder.

A solution of 1,1"-dihexyl-2',6'-di-p-tolyl-[4,1':4',4"-terpyridine]-1,1',1"-triium tetrafluoroborate diiodide (1.06 g, 1.1 mmol) in MeOH (5 mL) was added dropwise to a solution of NaBF₄ (2.25 g, 20.4 mmol) in water (35 mL) with rapid stirring. The resulting mixture was heated, cooled with rapid stirring and decanted. The residue was dissolved in MeOH (10 mL) and water (40 mL) was added with rapid stirring. The resulting precipitate was filtered, dissolved in MeOH (10 mL) and water (40 mL) was added with rapid stirring. The solvent was reduced in volume and decanted. The residue was dissolved in MeCN (2 mL) and Et₂O (25 mL) added. The resulting precipitate was filtered, washed with Et₂O and air dried to give the 1,1"-dihexyl-2',6'-di-p-tolyl-[4,1':4',4"-terpyridine]-1,1',1"-triium tris(tetrafluoroborate) (0.10 g, 9%) as brown powder.

$\delta_H$ (400 MHz CD₃OD) 9.24 (2H, d, J=6.4 Hz), 9.02 (2H, d, J=6.4 Hz), 8.82 (s, 2H), 8.73 (2H, d, J=6.4 Hz), 8.24 (2H, d, J=6.4 Hz), 7.45 (4H, d, J=8 Hz), 7.28 (4H, d, J=8 Hz), 4.74 (2H, t, J=7.6 Hz), 4.58 (2H, t, J=7.6 Hz), 2.34 (s, 6H), 2.16-2.04 (m, 2H), 1.92-1.77 (m, 2H), 1.53-1.24 (m, 10H), 1.14-1.02 (m, 2H) and 0.98-0.88 (m, 6H).

$\delta_F$ (376 MHz CD₃OD) −153.25−−153.43.

Example 6: Synthesis of 2',6'-bis(4-fluorophenyl)-1,1"-dihexyl-[4,1':4',4"-terpyridine]-1,1',1"-triium tris(tetrafluoroborate)

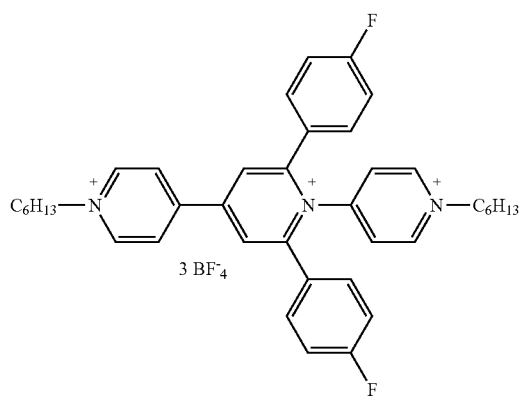

Ground NaOH (11.22 g, 280.5 mmol) was added portionwise to a mixture of 4'-fluoroacetophenone (38.7 g, 280 mmol) and pyridine-4-carboxaldehyde (15.00 g, 140 mmol) with grinding. Grinding was continued for 5 min and the solid mass was suspended in hot MeOH/water (600 mL, 1:2) with stirring. The mixture was heated for 0.5 h, cooled, extracted with EtOAc (2×200 mL), washed with water (200 mL), dried (Na₂SO₄), and the solvent removed under reduced pressure. The residue was triturated twice with EtOAc/hexanes, filtered, washed with hexanes and air dried to give 1,5-bis(4-fluorophenyl)-3-(4-pyridyl)pentane-1,5-dione (37.33 g, 73%) as tan powder. trans-Chalcone (7.27 g, 35 mmol) and the foregoing tan powder (12.27 g, 33.6 mmol) were dissolved in hot AcOH (30 mL) under N₂. BF₃.Et₂O (69 mL) was added dropwise with stirring and heating was continued for 6 h. The resulting mixture was cooled, diluted with Et₂O (500 mL), decanted, and the residue triturated with Et₂O (3×250 mL), filtered, washed with Et₂O (100 mL) and air dried to give 4-[2,6-bis(4-fluorophenyl)pyrylium-4-yl)pyridin-1-ium bis(tetrafluoroborate) 16.72 g (95%) as an ochre powder.

A solution of 4-[2,6-bis(4-fluorophenyl)pyrylium-4-yl]pyridin-1-ium bis(tetrafluoroborate) (4.06 g, 7.8 mmol), 4-aminopyridine (0.88 g, 9.3 mmol), NaOAc (2.56 g, 31.2 mmol) in propan-2-ol (60 mL) was heated at reflux for 16 h, cooled, the solvent removed under reduced pressure and the residue chromatographed on neutral alumina using MeOH (10% in EtOAc) as eluent. The fractions containing a fluorescent band were collected and the solvent removed under reduced pressure to give the product (0.92 g) as pale yellow powder with an unknown counter-ion. A solution of the foregoing yellow powder (0.80 g, 1.6 mmol), 1-iodohexane (3.98 g, 18.8 mmol) in MeCN (30 mL) under N₂ was heated at reflux for 2 days, cooled and the solvent was reduced in volume. Et₂O (40 mL) was added and the resulting precipitate filtered, washed with Et₂O and air dried. The resulting brown powder was dissolved in MeOH (40 mL) and added dropwise to a solution of NaBF₄ (10.35 g, 94 mmol) in water (50 mL) with rapid stirring. Stirring was continued for 0.5 h and the solvent reduced in volume. The resulting precipitate was filtered, washed with water and air dried. The resulting solid was washed with EtOAc, filtered and air dried. Crystallisation from MeOH at 0° C. gave 2',6'-bis(4-fluorophenyl)-1,1"-dihexyl-[4,1':4',4"-terpyridine]-1,1',1"-triium tris(tetrafluoroborate) (0.41 g, 31%) as tan powder.

$\delta_H$ (400 MHz CD₃OD) 9.26 (2H, br. d, J=5.2 Hz), 9.06 (2H, br. d, J=5.2 Hz), 8.91 (br.s, 2H), 8.74 (2H, br. d, J=5.2 Hz), 8.25 (2H, br. d, J=5.2 Hz), 7.71-7.58 (br. m, 4H), 7.30-7.14 (br. m, 4H), 4.74 (2H, br. t, J=6.8 Hz), 4.58 (2H, br. t, J=6.8 Hz), 2.17-2.03 br. (m, 2H), 1.95-1.80 (br. m, 2H), 1.53-1.20 (br. m, 10H), 1.14-1.00 (br. m, 2H) and 0.98-0.84 (br. m, 6H).

$\delta_F$ (376 MHz CD₃OD) −108.54, −153.10−−153.40.

Example 7: Synthesis of 4,4'-(1,2-phenylene)bis[1-(2-isopropylphenyl)pyridin-1-ium] bis(tetrafluoroborate)

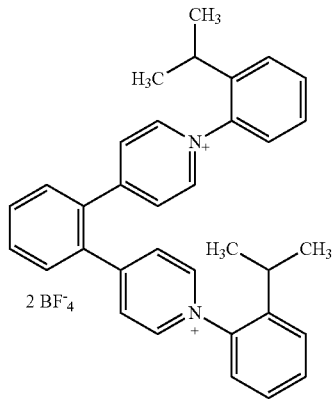

A mixture of 4-(4,4,5,5-tetramethyl-1,3,2-dioxaborolan-2-yl)pyridine (6.51 g, 31.8 mmol), 1,2-dibromobenzene (3.00 g, 12.7 mmol), K₂CO₃ (4.38 g, 31.8 mmol) and Pd(PPh₃)₄ (0.52 g, 3.5 mol %) in degassed EtOH (30 mL) and PhMe (30 mL) under N₂ was heated at reflux for 12 days, cooled, poured into water (100 mL), extracted with dichloromethane (4×50 mL), dried (Na₂SO₄) and the solvent removed under reduced pressure. The residue was chromatographed on silica using MeOH (0-3% in DCM) as eluent. The solvent was removed under reduced pressure and the residue crystallised from hot EtOAc/hexanes to give tan needles (2.15 g). The solvent was reduced to give a second crop (0.29 g). The two crops were combined, dissolved in dichloromethane (100 mL), extracted with HCl (2 M, 2×100 mL), neutralised with NaOH (2 M), extracted with dichloromethane (3×100 mL), dried (Na$_2$SO$_4$) and the solvent removed under reduced pressure. The residue was crystallised from EtOAc/hexanes to give the 1,2-bis(4-pyridyl)benzene (1.66 g, 56%) as colourless prisms. The filtrate was reduced in volume to give a second crop (0.43 g, 14%). A mixture of 1,2-di(4-pyridyl)benzene (1.00 g, 4.3 mmol) and 2,4-dinitrophenyl p-toluenesulfonate (3.64 g, 10.8 mmol) in MeCN (40 mL) was heated at reflux for 16 h under N$_2$ with stirring. The resulting precipitate was filtered, washed with MeCN (10 mL) and air dried to give the 4,4'-(1,2-phenylene)bis[1-(2,4-dinitrophenyl)pyridin-1-ium] bis(p-toluenesulfonate) (3.20 g, 82%) as a pale yellow powder.

A solution of 4,4'-(1,2-phenylene)bis[1-(2,4-dinitrophenyl)pyridin-1-ium] bis(p-toluenesulfonate) (3.00 g, 3.3 mmol) in hot MeOH (20 mL) was added dropwise to a solution of NaBF$_4$ in water (10 mL) with stirring. The resulting precipitate was filtered, washed with water (10 mL), dissolved in hot MeOH (20 mL) and added dropwise to a solution of NaBF$_4$ in water (10 mL), stirred hot for 10 min and then cooled. The precipitate was filtered off, washed with water (10 mL) and air dried to give 4,4'-(1,2-phenylene)bis[1-(2,4-dinitrophenyl)pyridin-1-ium] bis(tetrafluoroborate) (2.33 g, 95%) as a pale yellow powder.

A solution of 4,4'-(1,2-phenylene)bis[1-(2,4-dinitrophenyl)pyridin-1-ium] tetrafluoroborate (1.4 g, 1.9 mmol) and 2-isopropylaniline (1.53 g, 11.3 mmol) in MeOH (30 mL) was heated at reflux for 24 h, then cooled. The solvent was removed under reduced pressure and the residue triturated 3 times with hot EtOH. Upon cooling filtration gave 4,4'-(1,2-phenylene)bis[1-(2-isopropylphenyl)pyridin-1-ium] bis(tetrafluoroborate) (1.04 g, 85%) as a cream powder.

$\delta_H$ (400 MHz DMSO-d$_6$) 9.21 (4H, d, J=6.4 Hz), 8.220 (4H, d, J=6.4 Hz), 8.00-7.87 (m, 4H), 7.77-7.66 (m, 4H), 7.61-7.48 (m, 4H), 2.45-2.33 (m, 2H), and 1.135 (12H, d, J=6.8 Hz).

$\delta_F$ (376 MHz DMSO-d$_6$) −148.11--148.37.

Example 8: Synthesis of 1,1"-dihexyl-4',6'-di-p-tolyl-[4,1':2',4"-terpyridine]-1,1',1"-triium tris(tetrafluoroborate)

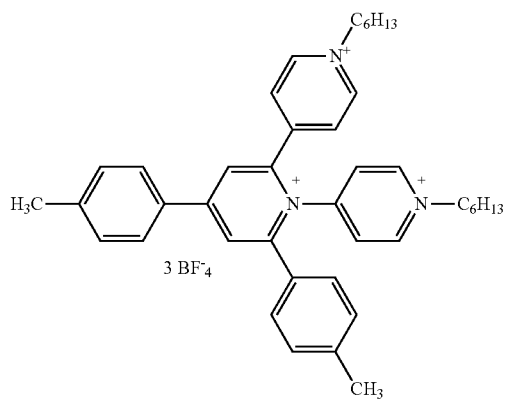

A mixture of 4,4'-dimethylchalcone (8.00 g, 33.9 mmol) and ground NaOH (1.36 g, 34 mmol) was ground for 20 min; the residue was dissolved in MeOH (200 mL), poured into water (200 mL) and extracted with dichloromethane (4×200 mL). After drying (Na$_2$SO$_4$) the solvent was removed under reduced pressure. The residue was chromatographed on silica using MeOH (0-3% in DCM) as eluent. The second band was collected and the solvent removed under reduced pressure to give 1-(4-pyridyl)-3,5-di-p-tolylpentane-1,5-dione (6.36 g) as a pale yellow powder.

BF$_3$.Et$_2$O (30 mL) was added dropwise to a refluxing solution 1-(4-pyridyl)-3,5-di-p-tolylpentane-1,5-dione (6.36 g, 17.8 mmol) and trans-chalcone (4.22 g, 20.3 mmol) in AcOH (13 mL) under N$_2$. Heating was continued for 6 h then the mixture was cooled, diluted with Et$_2$O (150 mL) and stirred for 10 min and filtered. The residue was triturated twice with hot AcOH, cooled and the precipitated product filtered and washed with Et$_2$O (4×50 mL) and air dried to give 2-(4,6-di-p-tolylpyrylium-4-yl)pyridin-1-ium bis(tetrafluoroborate) (5.92 g, 65%) as an orange powder.

A solution of 2-(4,6-di-p-tolylpyrylium-4-yl)pyridin-1-ium bis(tetrafluoroborate) (4.00 g, 7.8 mmol), 4-aminopyridine (0.88 g, 9.3 mmol), NaOAc (2.56 g, 31.2 mmol) in propan-2-ol (60 mL) was heated at reflux for 16 h, cooled and water (100 mL) added. The solvent was reduced in volume and the resulting precipitate filtered, washed with water (2×50 mL) and air dried to give 4',6'-di-p-tolyl-[4,1':2',4"-terpyridin]-1'-ium tetrafluoroborate (3.64 g, 93%) as a tan powder.

A solution of 4',6'-di-p-tolyl-[4,1':2',4"-terpyridin]-1'-ium tetrafluoroborate (1.20 g, 2.4 mmol), 1-iodohexane (6.09 g, 28.7 mmol) in MeCN (30 mL) under N$_2$ was heated at reflux for 2 days, cooled and the volume of the solvent reduced. Et$_2$O (40 mL) was added and the resulting precipitate filtered, washed with Et$_2$O (3×30 mL) and air dried. The resulting orange powder was dissolved in MeOH (20 mL) and added dropwise to a solution of NaBF$_4$ (15.80 g, 144 mmol) in water (30 mL) with rapid stirring. The mixture was heated to dissolution, cooled and the volume of the solvent reduced. The resulting precipitate was filtered, dissolved in hot MeOH (10 mL) and added dropwise to NaBF$_4$ (15.80 g, 144 mmol) in water (150 mL) with rapid stirring. The resulting precipitate was filtered off, washed with water (2×50 mL) and air dried to give 1,1"-dihexyl-4',6'-di-p-tolyl-[4,1':2',4"-terpyridine]-1,1',1"-triium tris(tetrafluoroborate) (1.71 g, 85%) as a yellow powder.

$\delta_H$ (400 MHz DMSO-d$_6$) 9.19 (2H, d, J=6.4 Hz), 9.08 (d, 2H, 6.8 Hz), 8.96-8.89 (m, 2H), 8.38 (2H, d, J=6.8 Hz), 8.32 (2H, d, J=8.0 Hz), 8.23 (2H, d, J=6.4 Hz), 7.54 (2H, d, J=8.0 Hz), 7.36 (2H, d, J=8.0 Hz), 7.26 (2H, d, J=8.0 Hz), 4.60 (2H, t, J=7.2 Hz), 4.52 (2H, t, J=6.8 Hz), 2.46 (s, 3H), 2.29 (s, 3H), 1.94-1.81 (m, 2H), 1.80-1.69 (m, 2H), 1.33-1.14 (m, 10H) and 0.99-0.80 (m, 8H).

$\delta_F$ (376 MHz DMSO-d$_6$) −148.17--148.34.

Example 9: Synthesis of 4,4'-(1,2-phenylene)bis(1-hexylpyridin-1-ium) bis(tetrafluoroborate)

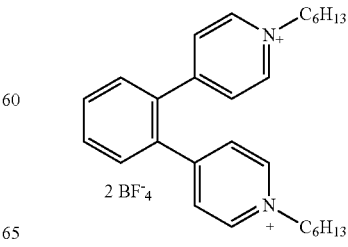

A solution of 1,2-di(4-pyridyl)benzene (0.61 g, 2.6 mmol) and 1-iodohexane (3.34 g, 15.8 mmol) in MeCN (40 mL) under $N_2$ in the dark was heated at reflux for 16 h. After cooling, the solvent was removed under reduced pressure. The residue was triturated with $Et_2O$ (3×30 mL) and air dried to give 1.67 g of a tan powder. The latter was dissolved in MeOH (5 mL) and added dropwise to a solution of $NaBF_4$ (1.73 g, 15.8 mmol) in water (30 mL) with stirring. Stirring was continued for 0.5 h, the resulting precipitate filtered, washed with water (2×15 mL) and dissolved in hot water (200 mL). Following filtration through a filter paper, the solution was cooled and $NaBF_4$ (1.73 g, 15.8 mmol) in water (100 mL) added with stirring. The resulting precipitate was filtered, washed with water (15 mL) and air dried to give 4,4'-(1,2-phenylene)bis(1-hexylpyridin-1-ium) bis(tetrafluoroborate) (0.90 g, 60%) as a pale yellow powder.

$\delta_H$ (400 MHz DMSO-$d_6$) 8.95 (4H, d, J=6.4 Hz), 7.97 (4H, d, J=6.4 Hz), 7.86-7.72 (m, 4H), 4.540 (4H, t, J=7.6 Hz), 1.95-1.79 (m, 4H), 1.35-1.20 (m, 12H) and 0.86 (6H, t, J=6.4 Hz).

$\delta_F$ (376 MHz DMSO-$d_6$) −148.10--148.34.

Example 10: Synthesis of 4,4'-(5,6,8,9-tetrahydrodibenzo[c,h]acridine-14-ium-7,14-diyl)bis(1-hexylpyridin-1-ium) tris(tetrafluoroborate)

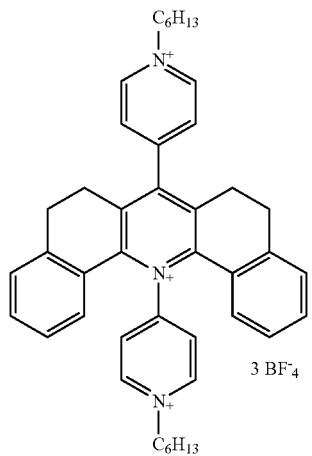

A solution of 4-(5,6,8,9-tetrahydrodibenzo[c,h]xanthen-14-ium-7-yl)pyridin-1-ium tetrafluoroborate (A. Kanitz, M. Maleika, W. Roth D E 10 2012 201 673) (4.18 g, 7.8 mmol), 4-aminopyridine (0.88 g, 9.3 mmol), NaOAc (2.56 g, 31.2 mmol) in propan-2-ol (60 mL) was heated at reflux for 16 h, cooled and water (200 mL) added, the resulting precipitate was filtered, washed with water (2×30 mL) and air dried. The solid was triturated with hot EtOH (30 mL), cooled, filtered, washed with EtOH and air dried to give 7,14-di(4-pyridyl)-5,6,8,9-tetrahydrodibenzo[c,h]acridin-14-ium tetrafluoroborate (2.59 g, 63%) as a fluorescent lime green powder.

A solution of 7,14-di(pyridin-4-yl)-5,6,8,9-tetrahydrodibenzo[c,h]acridin-14-ium tetrafluoroborate (1.00 g, 1.9 mmol) and 1-iodohexane (4.84 g, 22.8 mmol) in MeCN (40 mL) in the dark under $N_2$ was heated at reflux for 2 days. After cooling, the solvent was reduced in volume, the mixture was diluted with $Et_2O$ and the resulting precipitate filtered, washed with $Et_2O$ (3×30 mL) and air dried to give 1.64 g of a red powder. The latter was dissolved in the minimum of MeOH (10 mL) and added dropwise to a solution of $NaBF_4$ (12.57 g, 114 mmol) in water (80 mL) with rapid stirring. Stirring was continued for 0.5 h after which time the resulting precipitate was collected by filtration. The precipitate was dissolved in water (1.5 L) and the solution filtered through celite. $NaBF_4$ (12.57 g, 114 mmol) was added to the filtrate with stirring. Stirring was continued for 10 min after which the resulting precipitate was collected by filtration. The precipitate was dissolved in MeOH (20 mL) and added dropwise to $NaBF_4$ (12.57 g, 114 mmol) in water (100 mL) with stirring. The resulting precipitate was filtered, washed with water (2×5 mL) and air dried. The precipitate was suspended in propan-2-ol (20 mL), heated, the solvent decanted and the residue dissolved in the minimum of hot MeOH. Propan-2-ol (30 mL) was added to the foregoing methanolic solution and the resulting precipitate was filtered and washed with propan-2-ol (2×5 mL) and air dried to give 4,4'-(5,6,8,9-tetrahydrodibenzo[c,h]acridine-14-ium-7,14-diyl)bis(1-hexylpyridin-1-ium) tris(tetrafluoroborate) (0.37 g, 22%) as a lime green fluorescent powder.

$\delta_H$ (400 MHz DMSO-$d_6$) 9.37 (2H, d, J=6.4 Hz), 9.30 (2H, d, J=6.8 Hz), 8.60 (2H, d, J=6.8 Hz), 8.34 (2H, d, J=6.4 Hz), 7.55 (2H, d, J=8.0 Hz), 7.46 (2H, dt, J=0.8 and 8 Hz), 7.06 (2H, dt, J=0.8 and 8.0 Hz), 6.52 (2H, d, J=8.0 Hz), 4.79-4.59 (m, 4H), 3.10-3.92 (m, 4H), 3.88-3.73 (m, 4H), 2.11-2.87 (m, 4H), 1.48-1.11 (m, 12H) and 0.97-0.81 (m, 6H).

$\delta_F$ (376 MHz DMSO-$d_6$) δ −148.13--148.32.

Example 11: Synthesis of 4,4',4'',4'''-(benzene-1,2,4,5-tetrayl)tetrakis(1-hexylpyridin-1-ium) tetrakis(tetrafluoroborate)

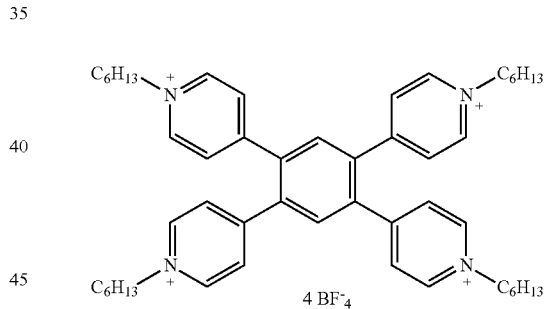

A mixture of 4-(4,4,5,5-tetramethyl-1,3,2-dioxaborolan-2-yl)pyridine (5.20 g, 25.4 mmol), 1,2,4,5-tetrabromobenzene (2.00 g, 5.1 mmol), $K_2CO_3$ (3.50 g, 25.4 mmol) and $Pd(PPh_3)_4$ (0.293 g, 5 mol %) in degassed EtOH (80 mL) and PhMe (80 mL) under $N_2$ was heated at reflux for 6 days. Additional 4-(4,4,5,5-tetramethyl-1,3,2-dioxaborolan-2-yl)pyridine (2.60 g, 12.7 mmol), $Pd(PPh_3)_4$ (0.293 g, 5 mol %) and $K_2CO_3$ (1.75 g, 12.7 mmol) were added and reflux continued for 2 days. The mixture was cooled and water (100 mL) was added and the mixture extracted with dichloromethane (2×200 mL). The extracts were washed with water (50 mL), dried ($Na_2SO_4$) and the solvent removed under reduced pressure. The residue was chromatographed twice on silica using MeOH (20-30% in EtOAc) as eluent. The fourth band was collected and the solvent removed under reduced pressure. The residue was dissolved in MeOH (10% in dichloromethane), filtered through a plug of silica and the solvent removed under reduced pressure. The residue was washed with EtOAc to give 1,2,4,5-tetra(4-pyridyl)

benzene (1.27 g, 65%) as colourless powder. The third fraction gave 4,4',4''-(benzene-1,2,4-triyl)tripyridine (0.05 g, 3%).

A solution of 1,2,4,5-tetra(4-pyridyl)benzene (0.40 g, 1 mmol) and 1-iodohexane (8.79 g, 41.5 mmol) in MeCN (60 mL) in the dark under $N_2$ was heated at reflux for 4 days. The mixture was cooled, diluted with $Et_2O$ and the resulting precipitate filtered. The residue was dissolved in hot MeCN, cooled and diluted with $Et_2O$. The product was filtered, washed with $Et_2O$ and air dried to give 4,4',4'',4'''-(benzene-1,2,4,5-tetrayl)tetrakis(1-hexylpyridin-1-ium) tetraiodide (1.02 g, 80%) as an orange powder.

A solution of 4,4',4'',4'''-(benzene-1,2,4,5-tetrayl)tetrakis(1-hexylpyridin-1-ium) tetraiodide (1.00 g, 0.8 mmol) in MeOH (5 mL) was added dropwise to a solution of $NaBF_4$ (2.85 g, 25.9 mmol) in water (20 mL) with stirring. Stirring was continued for 0.5 h and the resulting precipitate filtered, washed with water (3×5 mL) and air dried. The residue was crystallised from MeOH (20 mL) at −10° C., filtered, washed with cold MeOH (5 mL), $Et_2O$ (20 mL) and air dried to give 4,4',4'',4'''-(benzene-1,2,4,5-tetrayl)tetrakis(1-hexylpyridin-1-ium) tetrakis(tetrafluoroborate) (0.57 g, 65%) as a grey powder.

$\delta_H$ (400 MHz $CD_3OD$) 8.91 (8H, d, J=6.4 Hz), 8.17 (s, 2H), 8.06 (8H, d, J=6.4 Hz), 4.605 (8H, t, J=7.6 Hz), 2.15-2.00 (m, 8H), 1.52-1.30 (m, 24H) and 0.92 (12H, t, J=6.8 Hz).

$\delta_F$ (376 MHz $CD_3OD$) −153.31--153.39.

Example 12: Synthesis of 1,1''-dihexyl-[4,2':5',4''-terpyridine]-1,1''-diium bis(tetrafluoroborate)

A mixture of 4-(4,4,5,5-tetramethyl-1,3,2-dioxaborolan-2-yl)pyridine (4.64 g, 22.6 mmol), 2,5-dibromopyridine (2.44 g, 10 mmol), $Pd(PPh_3)_4$ (0.59 g, 0.51 mmol, 5 mol %) and $K_2CO_3$ (3.12 g, 22.6 mmol) in degassed EtOH (50 mL) and PhMe (50 mL) under $N_2$ was heated at reflux for 5 days, cooled, diluted with water (100 mL) and extracted with DCM (4×100 mL). The organic portions were dried with anhydrous sodium sulfate and the solvent removed in vacuo to yield a yellow solid, which was recrystallised from toluene/hexane to afford a pale brown solid (2.23 g). The solid was chromatographed on silica, eluting with 10% MeOH in ethyl acetate. The solvent was removed to yield 4,2':5',4''-terpyridine as a white powder (2.01 g, 86.1%).

The foregoing 4,2':5',4''-terpyridine (1.90 g, 8.15 mmol) was added to a stirred solution of 1-iodohexane (6.0 mL, 41 mmol) in MeCN (50 mL). The mixture was heated at reflux under $N_2$ in the dark for 3 days and then cooled to room temperature. The solvent was removed in vacuo to give a red solid, which was washed with $Et_2O$ to yield 1,1''-dihexyl-[4,2':5',4''-terpyridine]-1,1''-diium diiodide as a red powder (5.24 g, 97.8%).

A filtered solution of the preceding 1,1''-dihexyl-[4,2':5',4''-terpyridine]-1,1''-diium iodide (5.0 g, 7.61 mmol) in MeOH (100 mL) was added dropwise to a stirred solution of $NaBF_4$ (5.01 g, 45.7 mmol) in water (50 mL) and the mixture stirred for 0.5 h. The foregoing mixture was poured into a solution of $NaBF_4$ (2.51 g, 22.8 mmol) in water (200 mL) and the precipitate collected by filtration. The precipitate was dissolved in MeOH (200 mL), added slowly to a stirred solution of $NaBF_4$ (7.52 g, 68.5 mmol) in water (200 mL) and then filtered through celite and concentrated to precipitation. The precipitate was filtered and air dried, followed by drying overnight in a vacuum oven (60° C., 25 mbar) to yield 1,1''-dihexyl-[4,2':5',4''-terpyridine]-1,1''-diium bis(tetrafluoroborate) as a cream powder (3.53 g, 80.4%).

$\delta_H$ (400 MHz $CD_3OD$) 9.45 (1H, d, J=1.8 Hz), 9.12 (4H, m), 8.89 (2H, d, J=6.9 Hz), 8.69 (1H, dd, J=8.4, 2.4 Hz), 8.60 (3H, m), 4.70 (4H, t, J=7.6 Hz), 2.10 (4H, m), 1.43 (12H, m), 0.95 (6H, m).

$\delta_F$ (376 MHz $CD_3OD$) −153.53--154.58.

Example 13: Synthesis of 1,1''-dihexyl-1'-methyl-[4,2':5',4''-terpyridine]-1,1',1''-triium tris(tetrafluoroborate)

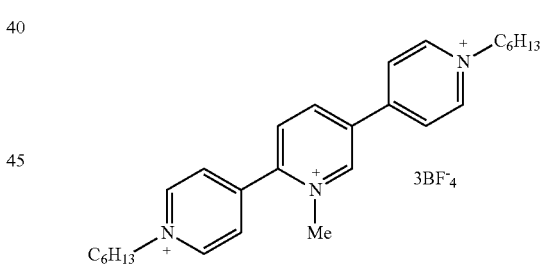

A mixture of the 1,1''-dihexyl[4,2':5',4''-terpyridine]-1,1''-diium tetrafluoroborate (2.50 g, 4.33 mmol) and $Me_3OBF_4$ (1.28 g, 8.66 mmol) in dichloromethane (60 mL) under $N_2$ was stirred at room temperature for 4 days. The precipitate was collected by filtration and then triturated with methanol. The resulting precipitate was collected by filtration and air dried to yield 1,1''-dihexyl-1'-methyl-[4,2':5',4''-terpyridine]-1,1',1''-triium tetrafluoroborate as a white powder (2.30 g, 78.2%).

$\delta_H$ (400 MHz DMSO-$d_6$) 10.01 (1H, s), 9.42 (5H, m), 8.20 (2H, d, J=6.4 Hz), 8.51 (3H, m), 4.75 (2H, t, J=7.3 Hz), 4.69 (2H, d, J=7.3 Hz), 4.30 (3H, s), 2.00 (4H, m), 1.33 (12H, bs), 0.91 (6H, m).

$\delta_F$ (376 MHz DMSO-$d_6$) −148.18--148.24.

Example 14 Synthesis of 4-[4-(1-hexylpyridin-1-ium-4-yl)phenyl]-1,2,6-tri-p-tolylpyridin-1-ium bis(tetrafluoroborate)

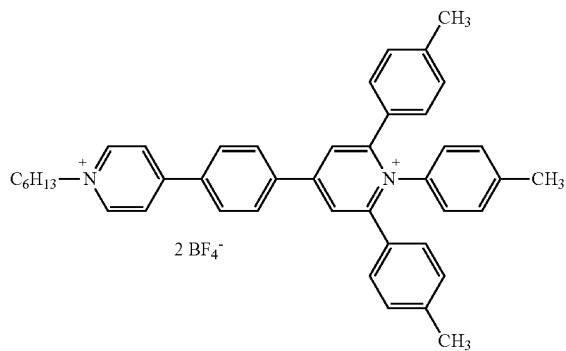

2 BF$_4^-$

Ground NaOH (0.87 g, 10.9 mmol) was added portionwise to a mixture of 4'-methylacetophenone (2.93 g, 21.9 mmol) and 4-(4-pyridyl)benzaldehyde (2.00 g, 10.9 mmol) with grinding. After 0.5 h water (50 mL) and EtOAc (50 mL) were added and the phases separated. The aqueous phase was extracted with EtOAc (50 mL) and the combined organic phases washed with water (50 mL) and dried (Na$_2$SO$_4$). The solvent was removed under reduced pressure. The residue was chromatographed on silica using EtOAc (70% in hexanes) as eluent. The fractions were evaporated under reduced pressure to give a gummy solid. Boron trifluoride etherate (16 mL) was added dropwise to a hot stirred solution of the solid and trans-chalcone (2.27 g, 10.9 mmol) in AcOH (7 mL) under N$_2$. The resulting solution was heated at reflux for 90 min, cooled and diluted with Et$_2$O (30 mL). The residue was filtered off and washed with Et$_2$O (3×50 mL) and air dried to give 4-[4-(2,6-di-p-tolylpyrylium-4-yl)phenyl]pyridin-1-ium bis(tetrafluoroborate) (1.94 g, 53%) as a yellow powder.

A solution of 4-[4-(2,6-di-p-tolylpyrylium-4-yl)phenyl]pyridin-1-ium bis(tetrafluoroborate) (0.80 g, 1.36 mmol), p-toluidine (0.21 g, 2 mmol), NaOAc (0.52 g, 6.3 mmol) in propan-2-ol (30 mL) was heated at reflux for 16 h, cooled and water (80 mL) added. The resulting precipitate was filtered off, washed with water (2×20 mL) and air dried. The solid was dissolved in EtOAc (40 mL) and poured into rapidly stirred hexanes (700 mL). The precipitated product was filtered off and washed with hexanes and air dried to give 4-[4-(pyridin-4-yl)phenyl]-1,2,6-tri-p-tolylpyridin-1-ium tetrafluoroborate (0.51 g, 64%) as cream-colored powder.

A solution of 4-[4-(pyridin-4-yl)phenyl]-1,2,6-tri-p-tolylpyridin-1-ium tetrafluoroborate (0.40 g, 0.68 mmol) and 1-iodohexane (0.43 g, 2 mmol) in MeCN (30 mL) in the dark, under N$_2$, was heated at reflux for 16 h after which the solvent was removed. The residue was washed with Et$_2$O (3×15 mL) and air dried to give 4-[4-(1-hexylpyridin-1-ium-4-yl)phenyl]-1,2,6-tri-p-tolylpyridin-1-ium iodide tetrafluoroborate (0.55 g, 98%) as a yellow powder.

A solution of 4-[4-(1-hexylpyridin-1-ium-4-yl)phenyl]-1,2,6-tri-p-tolylpyridin-1-ium iodide tetrafluoroborate (0.50 g, 0.62 mmol) in MeOH (5 mL) was added dropwise to NaBF$_4$ (0.68 g, 6.2 mmol) in water (30 mL) with stirring. Stirring was continued for 0.5 h and the resulting precipitate was filtered off, washed with water (2×2 mL) and air dried to give the title compound (0.47 g, 100%) as a yellow powder.

$\delta_H$ (400 MHz CD$_3$OD) 9.02 (2H, d, J=6.8 Hz), 8.49 (4H, m), 8.37 (2H, d, J=8.5 Hz), 8.26 (2H, d, J=8.5 Hz), 7.32 (4H, d, J=8.1 Hz), 7.17 (6H, m), 7.03 (2H, d, J=8.2 Hz), 6.64 (2H, t, J=7.5 Hz), 2.32 (6H, s), 2.22 (3H, s), 2.06 (2H, m), 1.40 (6H, m), 0.93 (3H, t, J=6.9 Hz).

$\delta_F$ (376 MHz CD$_3$OD) −154.32−−154.37.

Example 15 Synthesis of 1'-hexyl-4-[4-(1-hexylpyridin-1-ium-4-yl)phenyl]-2,6-di-p-tolyl-[1,4'-bipyridine]-1,1'-diium tris(tetrafluoroborate)

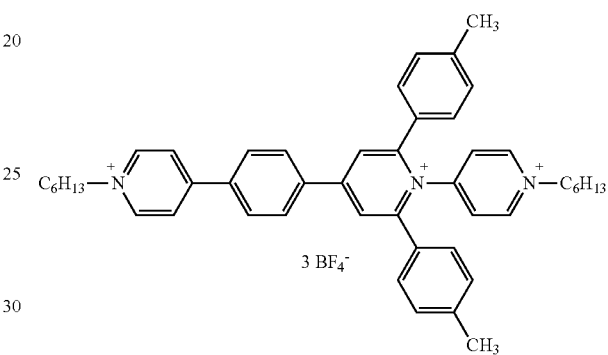

3 BF$_4^-$

A solution of 4-[4-(pyridin-4-yl)phenyl]-1,2,6-tri-p-tolylpyridin-1-ium tetrafluoroborate (1.09 g, 1.8 mmol), 4-aminopyridine (0.21 g, 22 mmol) and NaOAc (0.61 g, 7.4 mmol) in propan-2-ol (30 mL) was heated at reflux for 16 h, then cooled and water (60 mL) added. The resulting solution was poured into water (4 L) with stirring. The mixture was filtered through a pad of celite. The celite was then washed with MeOH (150 mL) and the methanol washings poured into water (3 L) with stirring. The resulting mixture was filtered through celite. The filtrates were combined and the solvent removed under reduced pressure. The residue was dissolved in MeOH-water (30 mL, 2:1) and added dropwise to a solution of NaBF (0.94 g, 10.8 mmol) in water (100 mL) with stirring. Stirring was continued for 0.5 h and the resulting precipitate filtered, washed with water and air dried to give 4-[4-(pyridin-4-yl)phenyl]-2,6-di-p-tolyl-[1,4'-bipyridin]-1-ium tetrafluoroborate (0.73 g, 68%) as pale yellow powder.

A solution of 4-[4-(pyridin-4-yl)phenyl]-2,6-di-p-tolyl-[1,4'-bipyridin]-1-ium tetrafluoroborate (0.60 g, 1 mmol) and 1-iodohexane (2.64 g, 12.4 mmol) in MeCN (25 mL) in the dark, under N$_2$, was heated at reflux for 3 days, then cooled and diluted with Et$_2$O (10 mL). The resulting precipitate was filtered, washed with Et$_2$O (3×10 mL) and air dried to give 1'-hexyl-4-[4-(1-hexylpyridin-1-ium-4-yl)phenyl]-2,6-di-p-tolyl-[1,4'-bipyridine]-1,1'-diium diiodide tetrafluoroborate (1.01 g, 97%) as an orange powder.

A solution of 1'-hexyl-4-[4-(1-hexylpyridin-1-ium-4-yl)phenyl]-2,6-di-p-tolyl-[1,4'-bipyridine]-1,1'-diium diiodide tetrafluoroborate (0.81 g, 0.81 mmol) in hot MeOH (50 mL) was added dropwise to NaBF$_4$ (1.78 g, 5.34 mmol) in water (50 mL) with stirring. The resulting mixture was heated to dissolution and then cooled. The precipitate was filtered off washed with water (3×20 mL) and air dried. The solid was recrystallised from hot MeOH (10 mL) and air dried to give the title compound (0.47 g, 63%) as a yellow powder.

$\delta_H$ (400 MHz (CD$_3$)$_2$CO) 9.21 (2H, d, J=6.5 Hz), 9.16 (2H, d, J=6.5 Hz), 8.73 (2H, s), 8.66 (2H, d, J=6.4 Hz), 8.53 (4H, m), 8.34 (2H, d, J=8.3 Hz), 7.52 (4H, d, J=8.0 Hz), 7.26 (4H, d, J=7.9 Hz), 4.84 (2H, t, J=7.5 Hz), 4.77 (2H, t, J=6.8 Hz), 2.15 (2H, m), 2.04 (6H, s), 1.96 (2H, m), 1.45 (2H, m), 1.34 (8H, m), 1.13 (2H, bm), 0.87 (6H, m).

$\delta_F$ (376 MHz (CD$_3$)$_2$CO) −150.99--151.05.

Example 16: Synthesis of 1,1''-dihexyl-2',6'-diphenyl-[4,1':4',4''-terpyridine]-1,1',1''-triium tris(tetrafluoroborate)

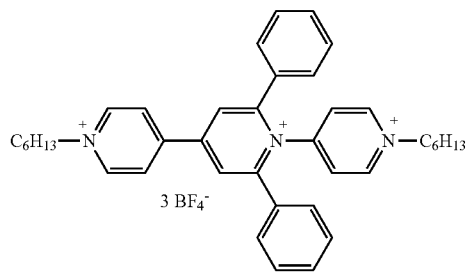

A solution of 4-(2,6-diphenylpyrylium-4-yl)pyridin-1-ium bis(tetrafluoroborate) bis(tetrafluoroborate) (C. Reichardt, D. Che, G. Heckenkemper and G. Schafer, *Eur. J. Org. Chem.*, 2001, 2343) (2.00 g, 4.2 mmol), 4-aminopyridine (0.48 g, 5.1 mmol), NaOAc (1.39 g, 16.9 mmol) in propan-2-ol (40 mL) was heated at reflux for 16 h, cooled and poured into water (2.5 L) with stirring. The resulting mixture was filtered through celite and the solvent removed under reduced pressure. The residue was dissolved in MeOH (10 mL) and added dropwise to a solution of NaBF$_4$ (13.86 g, 126 mmol) in water (250 mL) with stirring. Stirring was continued for 0.5 h and the resulting precipitate filtered, washed with water (2×5 mL) and air dried to give 2',6'-diphenyl-[4,1':4',4''-terpyridin]-1'-ium tetrafluoroborate (1.05 g, 52%) as a yellow powder.

A solution of 2',6'-diphenyl-[4,1':4',4''-terpyridin]-1'-ium tetrafluoroborate (0.80 g, 1.7 mmol) and 1-iodohexane (3.58 g, 16.9 mmol) in MeCN (40 mL) in the dark under N$_2$ was heated at reflux for 3 days. After cooling, the solvent was reduced and the residue triturated with Et$_2$O (3×10 mL). The resulting solid, dissolved in MeOH (10 mL), was added dropwise to NaBF$_4$ (4.46 g, 40.5 mmol) in water (200 mL) with stirring. The resulting mixture was heated to dissolution, filtered through filter paper and the solvent volume reduced to ca 100 mL. NaBF$_4$ (4.46 g, 40.5 mmol) was added and the resulting precipitate was filtered, washed with water (20 mL) and air dried to give 1,1''-dihexyl-2',6'-diphenyl-[4,1':4',4''-terpyridine]-1,1',1''-triium tris(tetrafluoroborate) (0.58 g, 42%) as a yellow powder.

$\delta_H$ (400 MHz CD$_3$OD) 9.23 (2H, d, J=6.4 Hz), 8.989 (2H, d, J=6.4 Hz), 8.85 (s, 2H), 8.71 (2H, d, J=6.4 Hz), 8.23 (2H, d, J=6.4 Hz), 7.64-7.37 (m, 10H), 4.37 (2H, t, J=7.6 Hz), 4.54 (2H, t, J=7.2 Hz), 2.18-1.99 (m, 2H), 1.90-1.75 (m, 2H), 1.53-1.18 (m, 10H), 1.12-0.98 (m, 2H), 0.98-0.84 (m, 6H).

$\delta_F$ (376 MHz CD$_3$OD) −153.08--153.27.

Example 17: Synthesis of 2',6'-bis(4-(trifluoromethyl)phenyl)-[4,1':4',4''-terpyridin]-1'-ium tetrafluoroborate

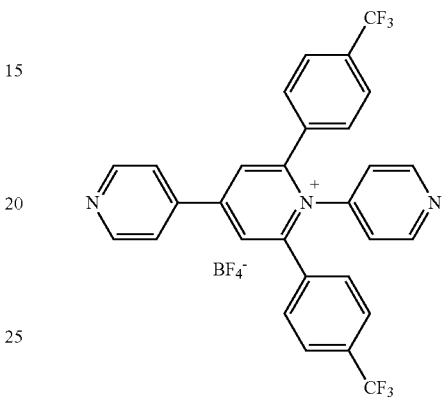

BF$_3$·Et$_2$O (14.6 g, 103 mmol) was added dropwise to a hot solution of 3-(4-pyridyl)-1,5-bis(4-(trifluoromethyl)phenyl) pentane-1,5-dione (E. L. Clennan, C. Liao and E. Ayokosok, *J. Am. Chem. Soc.*, 2008, 130, 7552) (6 g, 12.9 mmol) and trans-chalcone (2.95 g, 14.2 mmol) in AcOH (10 mL) was added. The resulting solution was heated at reflux for 6 h and the mixture was cooled, diluted with Et$_2$O (60 mL) and filtered. The residue was washed with Et$_2$O (50 mL) and air dried. The residue was triturated with hot AcOH (50 mL), cooled, filtered, washed with Et$_2$O (2×50 mL) and air dried to give 4-{2,6-bis[4-(trifluoromethyl)phenyl]pyrylium-4-yl}pyridin-1-ium bis(tetrafluoroborate) (5.43 g, 68%) as a yellow powder which turned green on standing and was used immediately in the next step.

A solution of 4-{2,6-bis[4-(trifluoromethyl)phenyl]pyrylium-4-yl}pyridin-1-ium bis(tetrafluoroborate) (5.43 g, 8.7 mmol), 4-aminopyridine (0.98 g, 10.4 mmol), NaOAc (2.87 g, 35 mmol) in propan-2-ol (40 mL) was heated at reflux for 16 h, cooled and diluted with water (200 mL). The precipitate was filtered and washed with water (2×50 mL). The residue was dissolved in MeOH (150 mL) and added dropwise to water (5 L) with stirring. The resulting mixture was filtered through celite and the solvent reduced in volume. The resulting precipitate was filtered, dissolved in MeOH (25 mL) and added dropwise to a solution of NaBF$_4$ (5.65 g, 51.4 mmol) in water (250 mL) with stirring. Stirring was continued for 0.5 h, the resulting precipitate filtered, washed with water and air dried to give 2',6'-bis(4-(trifluoromethyl)phenyl)-[4,1':4',4''-terpyridin]-1'-ium tetrafluoroborate (3.11 g, 58%) as a pale yellow powder.

$\delta_H$ (400 MHz CD$_3$OD) 8.84 (2H, d, J=5.6 Hz), 8.80 (s, 2H), 8.50 (2H, s, J=5.6 Hz), 8.14 (2H, d, J=5.6 Hz), 7.82-7.66 (m, 8H) and 7.53 (2H, d, J=5.6 Hz).

$\delta_F$ (376 MHz CD$_3$OD) −64.65, −153.16--153.27.

Example 18: Synthesis of 2',6'-di-p-tolyl-[4,1':4',4"-terpyridin]-1'-ium tetrafluoroborate

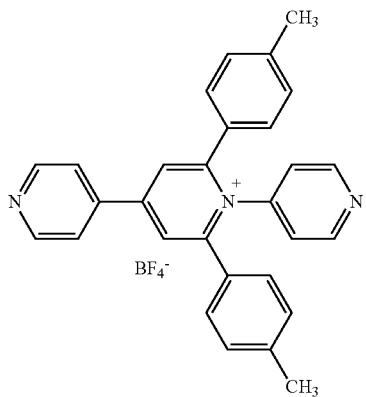

A solution of 4-[2,6-di(4-methylphenyl)pyrylium-4-yl]pyridin-1-ium bis(tetrafluoroborate) (S. Aiken, D. L. Crossley, C. D. Gabbutt, B. M. Heron, C. Biver, S. Archambeau and F. Berit-Debat, EP2848668A1) (4 g, 7.8 mmol), 4-aminopyridine (0.88 g, 9.3 mmol), NaOAc (2.56 g, 31.2 mmol) in propan-2-ol (60 mL) was heated at reflux for 16 h, cooled and water (100 mL) added. The solvent was removed and MeOH (100 mL) added. The resulting solution was diluted with water (4 L), the solvent reduced in volume and the sticky precipitate was filtered through celite. The solvent was removed under reduced pressure and the residue dissolved in MeOH (10 mL) and added dropwise to water (70 mL) with rapid stirring. Stirring was continued for 0.5 h and the resulting precipitate was filtered and air dried to give 2',6'-di-p-tolyl-[4,1':4',4"-terpyridin]-1'-ium tetrafluoroborate (2.67 g, 68%) as a yellow powder.

$\delta_H$ (400 MHz CD$_3$OD) 8.87 (2H, d, J=6.4 Hz), 8.66 (s, 2H), 8.48 (2H, d, J=6.4 Hz), 8.15 (2H, d, J=6.4 Hz), 7.45 (2H, d, J=6.4 Hz), 7.36 (4H, d, J=8.4 Hz) and 7.24 (4H, d, J=8.4 Hz).

$\delta_F$ (376 MHz CD$_3$OD) −154.31--154.44.

Example 19: Synthesis of 1,1"-dihexyl-4'-(1-hexylpyridin-1-ium-4-yl)-6'-(p-tolyl)-[4,1':2',4"-terpyridine]-1,1',1"-triium tetrakis(tetrafluoroborate)

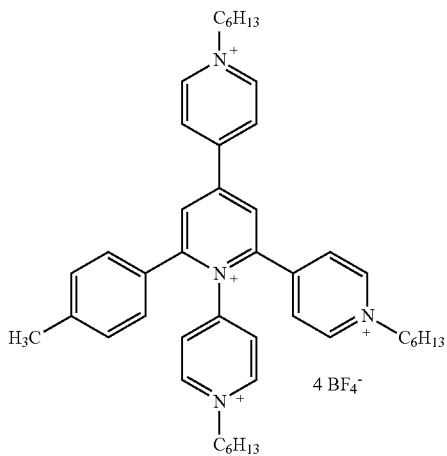

Sodium hydroxide (0.16 g, 4 mmol) in water (10 ml) was added to a solution of trans-3-(4-pyridyl)-1-(p-tolyl)prop-2-en-1-one (5.17 g, 23.2 mmol) and 4-acetylpyridine (2.81 g, 23.3 mmol) in MeOH (80 mL) at 0° C. with stirring. Stirring was continued at rt for 16 h. Water (100 mL) was added and the mixture extracted with dichloromethane (3×100 mL). The extracts were dried (Na$_2$SO$_4$) and the solvent removed under reduced pressure. The residue was chromatographed on silica using MeOH (10% in EtOAc) as eluent. The fraction with R$_f$=0.5 was collected and the solvent removed under reduced pressure to give 1,3-di(4-pyridyl)-5-(p-tolyl)pentane-1,5-dione (0.79 g, 10%) as a pale yellow gum which solidified on standing.

BF$_3$.Et$_2$O (23 g, 162 mmol) was added dropwise to a hot solution of 1,3-di(4-pyridyl)-5-(p-tolyl)pentane-1,5-dione (3.65 g, 10.6 mmol) and trans-chalcone (2.54 g, 12.2 mmol) in hot AcOH (9 mL) with stirring. The resulting solution was heated at reflux for 6 h and the mixture cooled, diluted with Et$_2$O (150 ml) and filtered. The residue was washed with Et$_2$O (2×50 mL) and air dried. The crude product was crystallised from hot AcOH (50 mL), filtered off and washed with AcOH (20 mL) and Et$_2$O (3×50 mL) and air dried to give 4,4'-[6-(p-tolyl)pyrylium-2,4-diyl]bis(pyridin-1-ium) tris(tetrafluoroborate) (3.75 g, 60%) as an orange powder which was used without further purification in the next step.

A solution of 4,4'-[6-(p-tolyl)pyrylium-2,4-diyl]bis(pyridin-1-ium) tris(tetrafluoroborate) (3.00 g, 5.1 mmol), 4-aminopyridine (0.57 g, 6 mmol), NaOAc (2.51 g, 30.6 mmol) in propan-2-ol (30 mL) was heated at reflux for 16 h, cooled and diluted with water (150 mL) and then poured into water (800 mL) with stirring. The resulting mixture was filtered through celite and the solvent removed under reduced pressure. The residue was dissolved in MeOH (30 mL) and water (40 mL) was added. The solvent was decanted and the residue air dried to give 4'-(4-pyridyl)-6'-(p-tolyl)-[4,1':2',4"-terpyridin]-1'-ium tetrafluoroborate (1.80 g, 72%) as a brown amorphous solid.

A solution of 4'-(4-pyridyl)-6'-(p-tolyl)-[4,1':2',4"-terpyridin]-1'-ium tetrafluoroborate (1.72 g, 3.5 mmol) and 1-iodohexane (6.72 g, 31.7 mmol) in MeCN (40 mL) under N$_2$ was heated at reflux in the dark for 2 days, cooled and filtered. The solvent was reduced in volume and the residue washed with Et$_2$O (2×80 mL). The product was filtered off and air dried. The product was dissolved in MeOH (150 mL) and added dropwise to a solution of NaBF$_4$ (6.20 g, 56 mmol) in water (1.5 L) with stirring. The resulting precipitate was filtered. The filtrand was dissolved in MeCN (40 mL) and added to Et$_2$O (500 mL) with rapid stirring. The resulting precipitate was filtered, washed with Et$_2$O (2×50 mL) and air dried to give the title compound (0.85 g, 32%) as a grey powder.

$\delta_H$ (400 MHz CD$_3$OD) 9.28 (2H, d, J=6.7 Hz), 9.06 (6H, m), 8.72 (2H, d, J=6.5 Hz), 8.27 (4H, d, J=4.7 Hz), 7.46 (2H, d, J=8.2 Hz), 7.30 (2H, d, J=8.1 Hz), 4.74 (2H, t, J=7.6 Hz), 4.58 (4H, m), 2.35 (3H, s), 1.99 (6H, m), 1.37 (18H, bm), 0.93 (9H, m).

$\delta_F$ (376 MHz CD$_3$OD) −152.92--152.97.

Example 20: Synthesis of 4,4'-{2-(p-tolyl)-5,6-dihydrobenzo[h]quinoline-1-ium-1,4-diyl}bis(1-hexylpyridin-1-ium) tris(tetrafluoroborate)

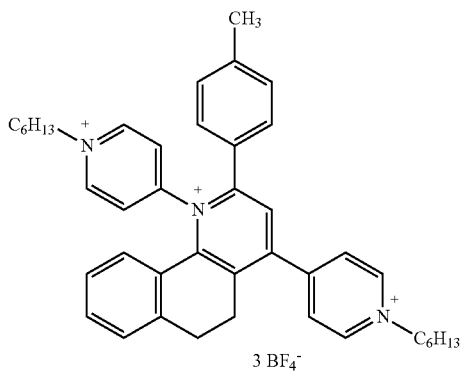

A mixture of trans-3-(4-pyridyl)-1-(p-tolyl)prop-2-en-1-one (2.50 g, 11.2 mmol) and NaOH (5.60 g, 140 mmol) were ground to a fine powder. 1-Tetralone (1.54 g, 11.2 mmol) was added and grinding continued for 20 min. The resulting gummy solid was taken up in warm EtOH (100 mL), diluted with water (100 mL) and extracted with dichloromethane (4×50 mL). The combined organic extracts were dried ($Na_2SO_4$) and the solvent removed under reduced pressure. The residue was crystallised from hot EtOH, filtered and air dried to give 2-[3-oxo-1-(4-pyridyl)-3-(p-tolyl)propyl]-3,4-dihydronaphthalen-1(2H)-one (0.96 g, 23%) as a light tan powder. The filtrate was evaporated under reduced pressure and the residue chromatographed on silica using EtOAc (25-80% in hexanes) as eluent. The band with $R_f$=0.6 (80% EtOAc in hexanes) was collected and the solvent removed under reduced pressure to give a second crop (1.77 g, 43%) as an orange gum which was combined with the aforementioned solid and used without further purification. $BF_3.Et_2O$ (12.3 mL, 87 mmol) was added dropwise to a hot solution of 2-[3-oxo-1-(4-pyridyl)-3-(p-tolyl)propyl]-3,4-dihydronaphthalen-1(2H)-one (2.73 g, 7.4 mmol) and trans-chalcone (1.74 g, 8.4 mmol) in hot AcOH (6 mL) with stirring. The resulting solution was heated at reflux for 3 h and the mixture cooled, diluted with $Et_2O$ (120 mL) and filtered. The residue was triturated with hot AcOH (40 mL). After cooling, the precipitate was collected by filtration and washed with AcOH (10 mL), $Et_2O$ (3×50 mL) and air dried to give 4-(2-(p-tolyl)-5,6-dihydrobenzo[I]chromen-1-ium-4-yl)pyridin-1-ium-2-ide bis(tetrafluoroborate) (2.84 g, 73%) as an orange powder.

A solution of 4-(2-(p-tolyl)-5,6-dihydrobenzo[h]chromen-1-ium-4-yl)pyridin-1-ium-2-ide bis(tetrafluoroborate) (2.61 g, 5 mmol), 4-aminopyridine (0.56 g, 6 mmol), NaOAc (1.63 g, 19.9 mmol) in propan-2-ol (40 mL) was heated at reflux for 16 h, cooled, diluted with water (2 L) and filtered through celite. The solvent was removed under reduced pressure, the residue dissolved in the minimum MeOH and added dropwise to a solution of $NaBF_4$ (1.64 g, 14.9 mmol) in water (200 mL) with stirring. Stirring was continued for 0.5 h, after which time the precipitate was collected by filtration washed with water (2×10 mL) and air dried to give 1,4-di(4-pyridyl)-2-(p-tolyl)-5,6-dihydrobenzo[h]quinolin-1-ium tetrafluoroborate (2.17 g, 85%) as a yellow powder.

A solution of the latter (1.50 g, 2.9 mmol) and 1-iodohexane (3.72 g, 17.5 mmol) in MeCN (40 mL) under $N_2$ was heated at reflux in the dark for 2 days. After cooling, the solvent was reduced in volume (ca. 20 mL), diluted with $Et_2O$ (50 mL) and filtered. The residue was washed with $Et_2O$ (3×30 mL) and air dried to give 4,4'-{2-(p-tolyl)-5,6-dihydrobenzo[h]quinoline-1-ium-1,4-diyl}bis(1-hexylpyridin-1-ium) bis(tetrafluoroborate) iodide (2.40 g, 88%) as a dark orange powder.

A solution of 4,4'-{2-(p-tolyl)-5,6-dihydrobenzo[h]quinoline-1-ium-1,4-diyl)bis(1-hexylpyridin-1-ium} bis(tetrafluoroborate) iodide (2.40 g, 2.6 mmol) in MeOH (20 mL) was added dropwise to $NaBF_4$ (1.69 g, 15 mmol) in water (150 mL) with stirring. The resulting precipitate was filtered, dissolved in MeOH (80 mL), added dropwise to a solution of $NaBF_4$ (33.8 g, 300 mmol) in water (2 L) with stirring. Stirring was continued for 0.5 h and the resulting precipitate filtered, washed with water (2×10 mL) and air dried to give the title compound (1.05 g, 48%) as a tan powder. The filtrate was reduced (ca. 150 mL), decanted, dissolved in MeOH (15 mL) and added dropwise to $NaBF_4$ (6.8 g, 62 mmol) in ice cold water (300 mL) with rapid stirring. The resulting precipitate was filtered, washed with water (2×5 mL) and air dried to give the title compound 4,4'-{2-(p-tolyl)-5,6-dihydrobenzo[h]quinoline-1-ium-1,4-diyl}bis(1-hexylpyridin-1-ium) tris(tetrafluoroborate) (0.84 g, 38%) as a yellow powder.

$\delta_H$ (400 MHz $CD_3OD$) 9.25 (d, 2H, J=6.8 Hz), 9.13 (d, 2H, J=6.8 Hz), 8.41 (s, 2H, J=5.6 Hz), 8.32 (s, 1H), 8.28 (d, 2H, J=6.8 Hz), 7.58-7.46 (m, 2H), 7.33 (d, 2H, J=8.4 Hz), 7.27 (d, 2H, J=8.4 Hz), 7.13 (t, 1H, J=7.2 Hz), 6.91 (d, 1H, J=8.4 Hz), 4.77 (t, 2H, J=7.6 Hz), 4.68 (t, 2H, J=7.2 Hz), 3.20-3.01 (m, 4H), 2.37 (s, 3H), 2.20-2.07 (m, 2H), 2.03-1.91 (m, 2H), 1.56-1.16 (m, 12H) and 1.02-0.91 (m, 6H).

$\delta_F$ (376 MHz $CD_3OD$) −153.61—153.75

Example 21: Synthesis of 1,1''-dihexyl-[4,2':3',4''-terpyridine]-1,1''-diium bis(tetrafluoroborate)

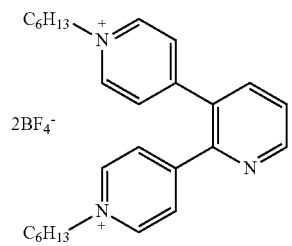

A mixture of 4-(4,4,5,5-tetramethyl-1,3,2-dioxaborolan-2-yl)pyridine (2.32 g, 11.3 mmol), 2,3-dibromopyridine (1.22 g, 5.0 mmol), $Pd(PPh_3)_4$ (0.30 g, 0.25 mmol, 5 mol %) and $K_2CO_3$ (1.56 g, 11.3 mmol) in degassed EtOH (25 mL) and PhMe (25 mL) under $N_2$ was heated at reflux for 10 days, cooled, diluted with water (100 mL) and extracted with dichloromethane (4×50 mL). The organic portions were dried with anhydrous sodium sulfate and solvent removed in vacuo to yield a brown oil which was chromatographed on silica, eluting with MeOH (10%) in ethyl acetate. The solvent was removed and the residue dissolved in hot hexane/ethyl acetate, decanted, cooled and the solvent removed to yield 4,2':3',4"-terpyridine as a pale orange oil (0.90 g, 77.2%).

1-Iodohexane (1.42 mL, 9.65 mmol) was added to a stirred solution of the foregoing 4,2':3',4"-terpyridine (0.38 g, 1.6 mmol) in MeCN (15 mL) and the mixture was heated at reflux under $N_2$ in the dark for 48 h. The reaction mixture was cooled and the precipitate collected by filtration and washed with $Et_2O$ to yield 1,1"-dihexyl-[4,2':3',4"-terpyridine]-1,1"-diiumdi iodide as a yellow/orange powder (1.00 g, 94.3%).

A filtered solution of the preceding 1,1"-dihexyl-[4,2':3',4"-terpyridine]-1,1"-diium diiodide (0.80 g, 1.27 mmol) in water:MeOH (3:7 mL) was added dropwise to a stirred solution of $NaBF_4$ (1.68 g, 15.3 mmol) in water (60 mL). The resulting mixture was stirred for 2 h and then the precipitate was collected by filtration. The precipitate was air dried to yield 1,1"-dihexyl-[4,2':3',4"-terpyridine]-1,1"-diium bis(tetrafluoroborate) as a yellow powder (0.47 g, 67.6%).

$\delta_H$ (400 MHz $CD_3OD$) 8.99 (1H, dd, J=4.8, 1.5 Hz), 8.93 (4H, m), 8.25 (1H, dd, J=7.9, 1.5 Hz), 8.10 (2H, d, J=6.7 Hz), 8.05 (2H, d, J=6.7 Hz), 7.83 (1H, dd, J=8.0, 4.8 Hz), 4.63 (4H, m), 2.05 (4H, m), 1.42 (12H, m), 0.94 (6H, m).

$\delta_F$ (376 MHz $CD_3OD$) −154.12--−154.18.

Example 22: Synthesis of 1,1"-dihexyl-1'-methyl-[4,2':3',4"-terpyridine]-1,1',1"-triium tris(tetrafluoroborate)

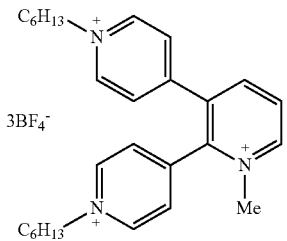

A mixture of the 1,1"-dihexyl-[4,2':3',4"-terpyridine]-1,1"-diium bis (tetrafluoroborate) (0.30 g, 0.55 mmol) and $Me_3OBF_4$ (0.12 g, 0.82 mmol) in dichloromethane (15 mL) under $N_2$ was stirred at rt for 4 days. The precipitate was collected by filtration and washed with MeOH and air dried to yield 1,1"-dihexyl-1'-methyl-[4,2':3',4"-terpyridine]-1,1',1"-triium tris(tetrafluoroborate) as a dull white powder (0.13 g, 37%).

$\delta_H$ (400 MHz DMSO-$d_6$) 9.46 (1H, d, J=5.8 Hz), 9.24 (2H, d, J=6.0 Hz), 9.03 (2H, d, J=6.1 Hz), 8.89 (1H, d, J=8.0 Hz), 8.59 (1H, app. t, J=6.9 Hz), 8.33 (2H, d, J=5.9 Hz), 7.98 (2H, d, J=6.0 Hz), 4.59 (4H, m), 4.16 (3H, s), 1.86 (4H, m), 1.28 (12H, m), 0.88 (6H, m).

$\delta_F$ (376 MHz DMSO-$d_6$) −148.19--−148.25.

Example 23: Synthesis of 1,1"-dihexyl-[4,2':4',4"-terpyridine]-1,1"-diium bis(tetrafluoroborate)

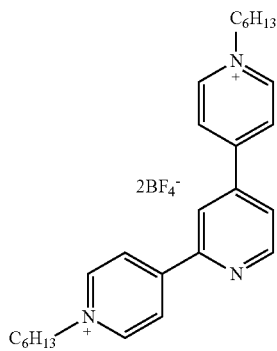

A mixture of 4-(4,4,5,5-tetramethyl-1,3,2-dioxaborolan-2-yl)pyridine (4.64 g, 22.6 mmol), 2,4-dibromopyridine (2.44 g, 10 mmol), $Pd(PPh_3)_4$ (0.59 g, 0.51 mmol, 5 mol %) and $K_2CO_3$ (3.12 g, 22.6 mmol) in degassed EtOH (50 mL) and PhMe (50 mL) under $N_2$ was heated at reflux for 5 days, cooled, diluted with water (100 mL) and extracted with dichloromethane (4×75 mL). The dried (anhydrous sodium sulfate) solvent was removed in vacuo and the resulting brown powder chromatographed on silica, eluting with 5-10% MeOH in ethyl acetate. The solvent was removed to yield 4,2':4',4"-terpyridine as an off-white solid (2.07 g, 88.7%).

1-Iodohexane (8.5 mL, 57.9 mmol) was added to stirred a solution of the foregoing 4,2':4',4"-terpyridine (1.90 g, 8.5 mmol) in MeCN (50 mL) and the mixture was heated at reflux under $N_2$ in the dark for 4 days. The reaction mixture was cooled and the resulting red precipitate was collected by filtration and washed with $Et_2O$ to yield 1,1"-dihexyl-[4,2':4',4"-terpyridine]-1,1"-diium diiodide as a yellow powder (3.80 g, 70.1%).

A filtered solution of the preceding 1,1"-dihexyl-[4,2':4',4"-terpyridine]-1,1"-diium diiodide (3.50 g, 5.32 mmol) in MeOH (15 mL) was added dropwise to a solution of $NaBF_4$ (9.34 g, 85.2 mmol) in water (400 mL). The resulting mixture was stirred for 2 h and then the precipitate of 1,1"-dihexyl-[4,2':4',4"-terpyridine]-1,1"-diium bis(tetrafluoroborate) was collected by filtration and air dried. To the supernatant was added $NaBF_4$ (2.33 g, 21.2 mmol) and the mixture was left overnight, after which time further precipitate was filtered and air dried to yield a second crop of 1,1"-dihexyl-[4,2':4',4"-terpyridine]-1,1"-diium bis(tetrafluoroborate) as a pale yellow powder (overall 2.33 g, 75.9%).

$\delta_H$ (400 MHz $CD_3OD$) 9.14 (2H, d, J=6.8 Hz), 9.09 (3H, m), 8.91 (2H, d, J=6.8 Hz), 8.85 (1H, d, J=0.5 Hz), 8.63 (2H, d, J=6.8 Hz), 8.15 (1H, dd, J=5.1, 1.6 Hz), 4.69 (4H, m), 2.08 (4H, m), 1.40 (12H, m), 0.92 (6H, m).

$\delta_F$ (376 MHz $CD_3OD$) −153.60--−153.69.

Example 24: Synthesis of 1,1''-dihexyl-1'-methyl-[4,2':4',4''-terpyridine]-1,1',1''-triium tris(tetrafluoroborate)

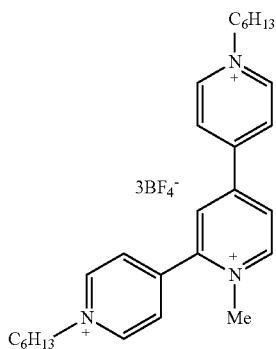

A mixture of the 1,1''-dihexyl-[4,2':4',4''-terpyridine]-1,1''-diium bis (tetrafluoroborate) (1.92 g, 3.50 mmol) and Me₃OBF₄ (0.77 g, 5.25 mmol) in dichloromethane (60 mL) under N₂ was stirred at rt for 3 days. The precipitate was collected by filtration and washed with MeOH. Crystallisation from MeOH yielded 1,1''-dihexyl-1'-methyl-[4,2':4',4''-terpyridine]-1,1',1''-triium tris(tetrafluoroborate) as a white powder (0.64 g, 28%).

$\delta_H$ (400 MHz DMSO-d₆) 9.55 (1H, d, J=6.6 Hz), 9.46 (2H, d, J=6.6 Hz), 9.42 (2H, d, J=6.8 Hz), 8.95 (1H, dd, J=6.4, 2.0 Hz), 8.88 (1H, d, J=1.9 Hz), 8.83 (2H, d, J=6.7 Hz), 8.55 (2H, d, J=6.6 Hz), 4.76 (2H, t, J=7.4 Hz), 4.69 (2H, t, J=7.5 Hz), 4.29 (3H, s), 2.00 (4H, bs), 1.35 (12H, bm), 0.90 (6H, m).

$\delta_F$ (376 MHz DMSO-d₆) −148.16−−148.22.

Example 25: Synthesis of 1,1',1''-trihexyl-[4,3':5',4''-terpyridine]-1,1',1''-triium tris(tetrafluoroborate)

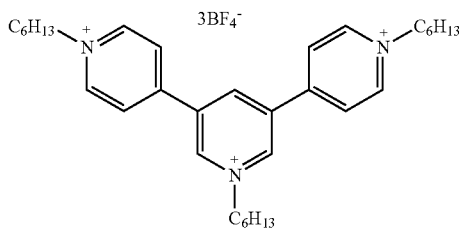

A mixture of 4-(4,4,5,5-tetramethyl-1,3,2-dioxaborolan-2-yl)pyridine (2.32 g, 11.3 mmol), 3,5-dibromopyridine (1.22 g, 5.0 mmol), Pd(PPh₃)₄ (0.30 g, 0.25 mmol, 5 mol %) and K₂CO₃ (1.56 g, 11.3 mmol) in degassed EtOH (25 mL) and PhMe (25 mL) under N₂ was heated at reflux for 3 days, cooled, diluted with water (100 mL) and extracted with DCM (4×25 mL). The organic portions were dried with anhydrous sodium sulfate and the solvent removed in vacuo to yield a white solid (1.29 g) which was chromatographed, eluting with 10% MeOH in ethyl acetate to yield 4,3':5',4''-terpyridine as a white solid (0.86 g, 73.7%).

1-Iodohexane (2.8 mL, 21 mmol) was added to a stirred solution of the foregoing 4,3':5',4''-terpyridine (0.70 g, 3.0 mmol) in MeCN (35 mL) and the mixture was heated at reflux under N₂ in the dark for 5 days. The reaction mixture was cooled and the precipitate was collected by filtration and washed with Et₂O to yield 1,1',1''-trihexyl-[4,3':5',4''-terpyridine]-1,1',1''-triium triiodide as an orange solid (2.36 g, 90.4%).

A filtered solution of the preceding 1,1',1''-trihexyl-[4,3':5',4''-terpyridine]-1,1',1''-triium triiodide (2.20 g, 2.53 mmol) in MeOH (15 mL) was added dropwise to a stirred solution of NaBF₄ (2.50 g, 22.8 mmol) in water (150 mL). The mixture was stirred for 0.5 h whereupon the precipitate was collected by filtration and air dried to yield 1,1',1''-trihexyl-[4,3':5',4''-terpyridine]-1,1',1''-triium tris(tetrafluoroborate) as an orange powder (1.58 g, 83.2%).

$\delta_H$ (400 MHz CD₃OD) 9.46 (1H, s), 9.34 (1H, dd, J=6.4, 1.0 Hz), 9.00 (4H, m), 8.43 (1H, d, J=6.3 Hz), 8.08 (4H, m), 4.78 (2H, t, J=7.7 Hz), 4.62 (4H, t, J=7.7 Hz), 2.15 (2H, m), 2.05 (4H, m), 1.51 (2H, m), 1.37 (16H, m), 0.92 (9H, m).

$\delta_F$ (376 MHz DMSO-d₆) −148.16−−148.22.

Example 26: Synthesis of 1,1',1''-trihexyl-[4,3':4',4''-terpyridine]-1,1',1''-triium tris(tetrafluoroborate)

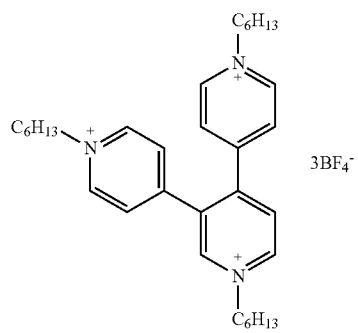

A mixture of 4-(4,4,5,5-tetramethyl-1,3,2-dioxaborolan-2-yl)pyridine (2.32 g, 11.3 mmol), 3,4-dibromopyridine (1.22 g, 5.0 mmol), Pd(PPh₃)₄ (0.30 g, 0.25 mmol, 5 mol %) and K₂CO₃ (1.56 g, 11.3 mmol) in degassed EtOH (25 mL) and PhMe (25 mL) under N₂ was heated at reflux for 7 days, cooled, diluted with water (50 mL) and extracted with DCM (4×75 mL). The organic portions were dried with anhydrous sodium sulfate and the solvent removed in vacuo to yield a red oil. The residue was chromatographed on silica, eluting with 5% MeOH in ethyl acetate to yield 4,3':4',4''-terpyridine as a cream powder (0.66 g, 56.4%).

1-Iodohexane (2.84 mL, 19.3 mmol) was added to a stirred solution of the foregoing 4,3':4',4''-terpyridine (0.50 g, 2.14 mmol) in MeCN (25 mL) and the mixture was heated at reflux under N₂ in the dark for 6 days. The reaction mixture was cooled and the solvent removed in vacuo and the residue triturated with Et₂O. The precipitate was collected by filtration, washed with Et₂O and air dried to yield 1,1',1''-trihexyl-[4,3':4',4''-terpyridine]-1,1',1''-triium triiodide as a metallic red powder (1.81 g, 97.3%).

A filtered solution of the preceding 1,1',1''-trihexyl-[4,3':4',4''-terpyridine]-1,1',1''-triium triiodide (1.50 g, 1.73 mmol) in MeOH (15 mL) was added dropwise to a stirred solution of NaBF₄ (2.36 g, 20.7 mmol) in water (175 mL). The mixture was stirred for 1 h, after which time the precipitated 1,1',1''-trihexyl-[4,3':4',4''-terpyridine]-1,1',1''-triium tris(tetrafluoroborate) was collected by filtration and air dried overnight. To the supernatant was added NaBF₄ (0.56 g, 5.16 mmol) and the mixture stirred for 4 h. The precipitate was collected by filtration and air dried overnight to give a second crop of 1,1',1''-trihexyl-[4,3':4',4''-terpyridine]-1,1',1''-triium tris(tetrafluoroborate) as a dark orange powder (overall 0.97 g, 75.2%).

$\delta_H$ (400 MHz CD$_3$OD) 9.46 (1H, s), 9.34 (1H, dd, J=6.4, 1.0 Hz), 9.00 (4H, m), 8.43 (1H, d, J=6.3 Hz), 8.08 (4H, m), 4.78 (2H, t, J=7.7 Hz), 4.62 (4H, t, J=7.7 Hz), 2.15 (2H, m), 2.05 (4H, m), 1.51 (2H, m), 1.37 (16H, m), 0.92 (9H, m).

$\delta_F$ (376 MHz CD$_3$OD) −153.12−−153.18.

Example 27: Synthesis of 1,1''-dihexyl-[4,2':6',4'']-terpyridine]-1,1''-diium bis(tetrafluoroborate)

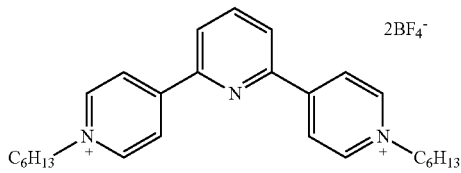

A mixture of 4-(4,4,5,5-tetramethyl-1,3,2-dioxaborolan-2-yl)pyridine (2.32 g, 11.3 mmol), 2,6-dibromopyridine (1.22 g, 5.0 mmol), Pd(PPh$_3$)$_4$ (0.30 g, 0.25 mmol, 5 mol %) and K$_2$CO$_3$ (1.56 g, 11.3 mmol) in degassed EtOH (25 mL) and PhMe (25 mL) under N$_2$ was heated at reflux for 5 days, cooled, diluted with water (50 mL) and extracted with DCM (2×25 mL). The organic portions were dried with anhydrous sodium sulfate and the solvent removed in vacuo to yield a white solid, which was crystallised from toluene/hexane to yield 4,2':6',4''-terpyridine as colourless crystals (1.05 g, 90%).

The foregoing 4,2':6',4''-terpyridine (0.47 mg, 2.0 mmol) was added to a stirred solution of 1-iodohexane (0.59 mL, 4.0 mmol) in MeCN (10 mL). The mixture was heated at reflux under N$_2$ in the dark for 48 hours, after which time further 1-iodohexane (0.30 mL, 2.0 mmol) was added and the mixture heated under reflux for a further 16 hours under N$_2$ in the dark. The cooled solvent was removed in vacuo to give a red solid, which was washed with Et$_2$O (15 mL) to yield 1,1''-dihexyl-[4,2':6',4'']-terpyridine]-1,1''-diium diiodide as an orange powder (1.22 g, 93%).

A filtered solution of the preceding 1,1''-dihexyl-[4,2':6',4'']-terpyridine]-1,1''-diium diiodide (1.00 g, 1.52 mmol) in MeOH:water (12:1 mL) was added dropwise to a stirred solution of NaBF$_4$ (2.00 g, 18.2 mmol) in water (125 mL). The mixture was stirred for 1 h whereupon the precipitate was collected by filtration and washed with a small amount of water and air dried to yield 1,1''-dihexyl-[4,2':4',4'']-terpyridine]-1,1''-diium bis(tetrafluoroborate) as a yellow powder (0.71 g, 75.9%).

$\delta_H$ (400 MHz DMSO-d$_6$) 9.27 (4H, d, J=6.8 Hz), 9.05 (4H, d, J=6.8 Hz), 8.69 (2H, d, J=7.9 Hz), 8.47 (1H, t, J=7.9 Hz), 4.68 (4H, t, J=7.3 Hz), 1.97 (4H, m), 1.30 (12H, m), 0.88 (6H, t, J=6.8 Hz).

$\delta_F$ (376 MHz DMSO-d$_6$) −148.17−−148.23.

Evaluation of Oxido-Reduction Potentials and Absorption Spectra of the Compounds of the Invention Method for Measuring Oxido-Reduction Potentials The oxido-reduction potentials of the compounds are measured by cyclic voltammetry with 3 electrodes.

The 3 electrodes used are:
1 Platinum working electrode
1 Platinum auxiliary or counter electrode
1 Platinum reference electrode which is immersed into a solution constituted of 0.01 M AgNO$_3$+0.1 M TBAP (tetrabutylammonium perchlorate) in acetonitrile.

The scan rate of the potential is fixed to 100 mV/s.

$E_1^{red}$ corresponds to the first reduction peak of the analyzed compound.

$E_2^{red}$ corresponds to the second reduction peak of the analyzed compound.

$E_1^{1/2}$ corresponds to the oxido-reduction potential of an oxidant/reductor system as calculated below:

$$E_1^{1/2}=(E_1^{red}+E_1^{ox})/2$$

wherein $E_1^{ox}$ corresponds to the first oxidation peak of the analyzed compound.

$\Delta E^{red}$ corresponds to the difference between $E_1^{red}$ and $E_2^{red}$ as calculated below:

$$\Delta E^{red}=|E_2^{red}|-|E_1^{red}|.$$

The indicated potential values are the first reduction potentials for the compounds, with respect to the standard hydrogen reference electrode (SHE).

The analyzed solution comprises 0.01 M of the compound to be analyzed and 1 M of TBAP salt in propylene carbonate as solvent.

Method for Measuring Absorption Spectra

The absorption spectra of the compounds are measured with a solution comprising 0.01 M of the compound to be analyzed, 0.02 M of 10-methylphenothiazine (Mephtz) and 1 M of TBAP salt in propylene carbonate as solvent.

This solution is introduced into a quartz cell where at least one glass electrode coated with Indium Tin Oxide (ITO) is placed in order to colour the analyzed compound on this electrode. The absorption spectrum of the compound in the time domain is measured by a spectrophotometer.

The reducing agent (10-methylphenothiazine for all compounds) colours on another glass electrode coated with Indium Tin Oxide (ITO).

The potential applied between both electrodes, for activating the compounds, is equal to the addition, in absolute value, of $E^1_{red}$ of the compound+$E^1_{ox}$ of methylphenothiazine (which has $E^1_{ox}$=0.45V).

The absorption spectrum is read after 3 min of activation, in particular the $\lambda_{max}$ value, which corresponds to the maximum absorption peak within the visible spectrum (between 400 and 800 nm).

The results for each of the synthesized compounds are indicated in Table 1 below. $E^1_{red}$ corresponds to the first reduction potential. The colour indicated in Table 1 is the visual colour perceived by emmetropic eyes under day light conditions. It should be noted that the $\lambda_{max}$ value just gives an approximate indication of the colour of a particular compound. However, as a consequence of the broad nature of the absorption bands, the whole absorption spectrum has to be taken into account in order to understand the final perceived colour of any one compound.

| Ref | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| 1 | C₆H₁₃—N⁺(pyridinium)—C₆H₄—N⁺(pyridinium)—C₆H₁₃ 2 BF₄⁻ | −1.28 | * | * | −1.21 | 556 | blue |
| 2 | C₆H₁₃—N⁺(pyridinium)—naphthalene—N⁺(pyridinium)—C₆H₁₃ 2 BF₄⁻ | −1.33 | * | * | −1.28 | 636 | pink |
| 3 | bis(2-isopropylphenyl) bipyridinium, 2 BF₄⁻ | −1.12 | * | * | −1.07 | 572 | brown |
| 4 | bis(2-isopropylphenyl) tetrafluoro-phenylene bipyridinium, 2 BF₄⁻ | −0.95 | * | * | −0.91 | 452 | purple |
| 5 | 2,6-bis(4-methylphenyl) terpyridinium trication, 3 BF₄⁻ | −0.57 | −1.20 | 0.63 | −0.53 | 542 | red |
| 6 | 2,6-bis(4-fluorophenyl) terpyridinium trication, 3 BF₄⁻ | −0.54 | −1.30 | 0.76 | −0.51 | 541 | red |

-continued

| Ref | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| 7 | 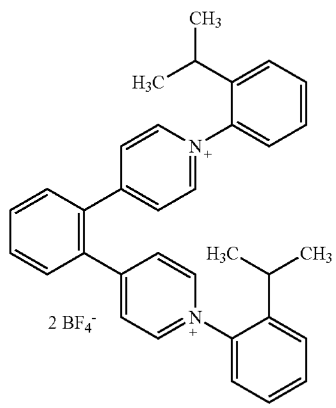 | −1.22 | * | * | −1.18 | 445 | yellow |
| 8 | 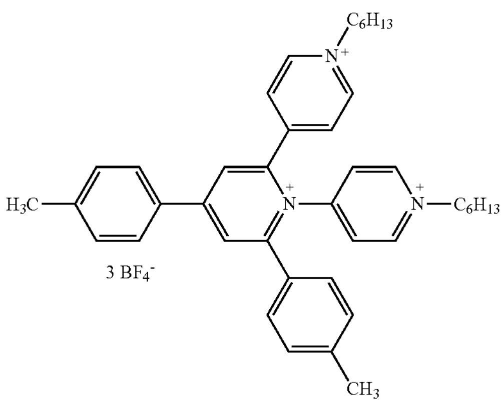 | −0.57 | −1.49 | 0.96 | −0.50 | 555 | purple |
| 9 | 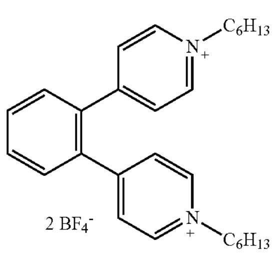 | −1.43 | * | * | −1.36 | 442 | yellow |
| 10 | 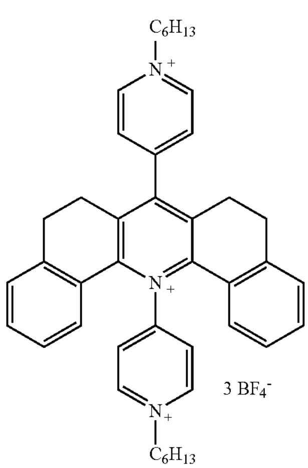 | −0.78 | −1.72 | 0.94 | −0.61 | 501 | red |

-continued
| Ref | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| 11 | 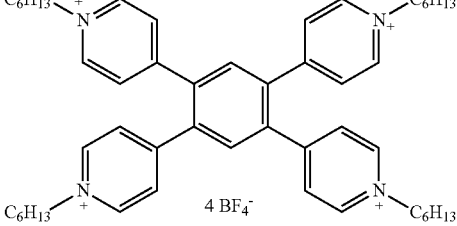 | −1.04 | −1.65 | 0.61 | −1.00 | 503 | green |
| 12 | 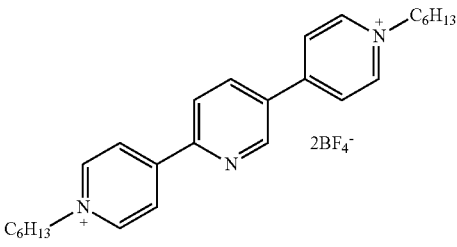 | −1.10 | −1.22 | 0.12 | −1.06 | 503 | khaki |
| 13 | 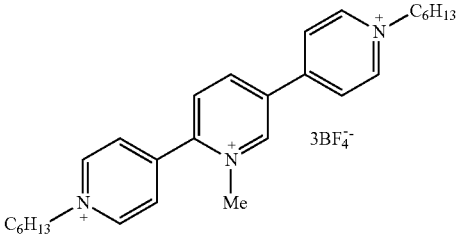 | −0.80 | −0.92 | 0.12 | −0.73 | 486 | brown |
| 14 | 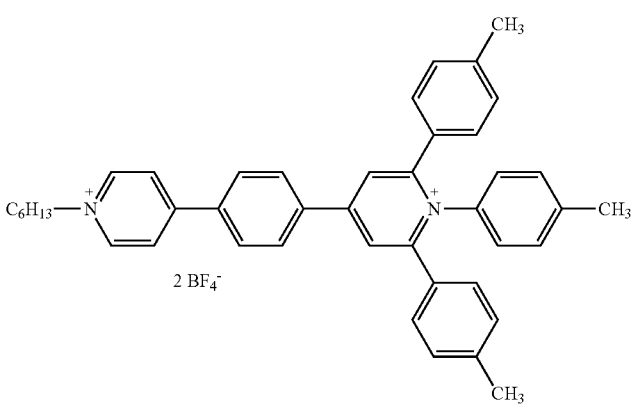 | −1.17 | * | * | −1.13 | 514 | grey green |
| 15 | 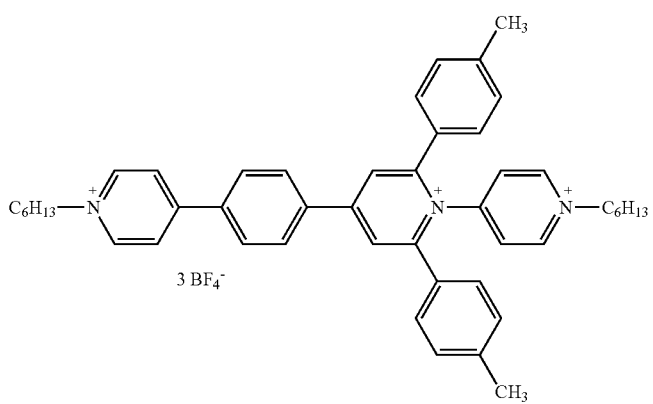 | −0.84 | * | * | −0.81 | 500 | slightly yellow |

-continued

| Ref | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| 16 | [structure with C₆H₁₃-pyridinium groups, phenyl substituents, 3 BF₄⁻] | −0.54 | * | * | −0.49 | 545 | red |
| 17 | [structure with CF₃-phenyl substituents, pyridyl groups, BF₄⁻] | −1.02 | * | * | −0.96 | 544 | red |
| 18 | [structure with CH₃-phenyl (tolyl) substituents, pyridyl groups, BF₄⁻] | −1.16 | * | * | −1.11 | 531 | red |
| 19 | [structure with C₆H₁₃-pyridinium groups, tolyl substituent, 4 BF₄⁻] | −0.33 | * | * | −0.27 | 641 | green |

-continued
| Ref | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| 20 | 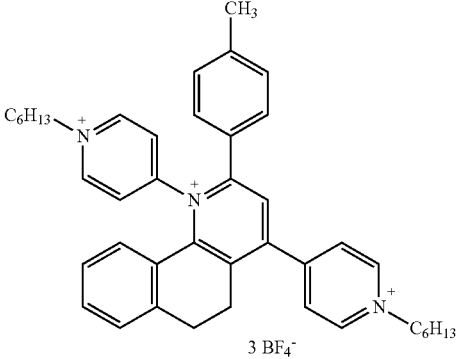 | −0.58 | * | * | −0.53 | 525 | red |
| 21 | 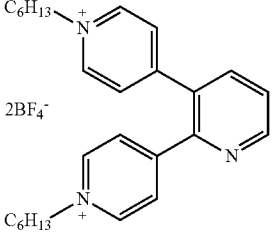 | −1.28 | * | * | −1.24 | 445 | green |
| 22 | 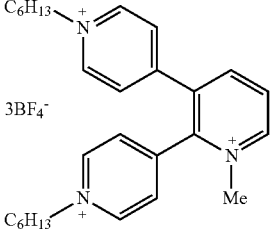 | −0.97 | −1.24 | 0.27 | −0.90 | 472 | orange brown |
| 23 | 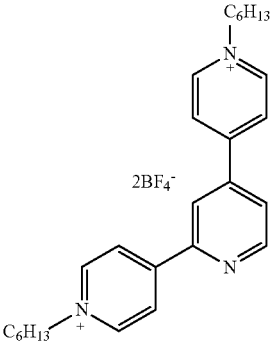 | −1.25 | −1.55 | 0.30 | −1.22 | 555 | purple |
| 24 | 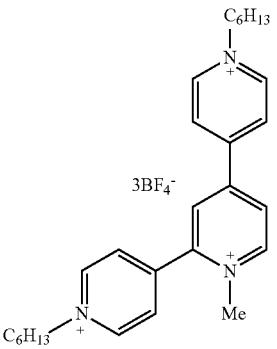 | −0.71 | −0.95 | 0.24 | −0.68 | 395 | blue |

| Ref | Structure | $E_1^{red}$ (V) | $E_2^{red}$ (V) | $\Delta E^{red}$ (V) | $E_1^{1/2}$ (V) | $\lambda_{max}$ (nm) | Color |
|---|---|---|---|---|---|---|---|
| 25 | 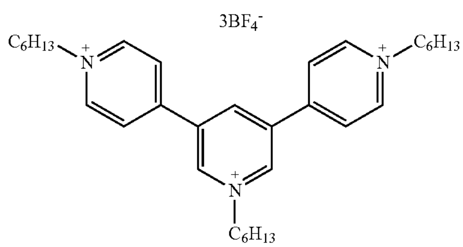 | −0.93 | * | * | * | 458 | red |
| 26 | 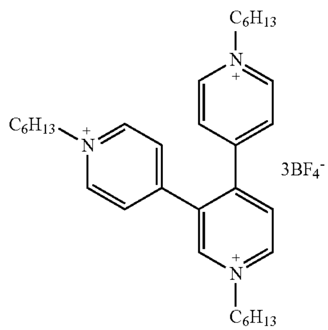 | −0.88 | * | * | * | 406 | green |
| 27 | 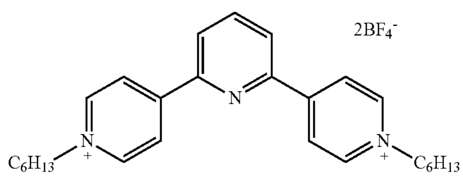 | −1.31 | −1.51 | 0.20 | −1.28 | 342 | deep purple |

The invention claimed is:

1. An electrochromic compound of formula (I):

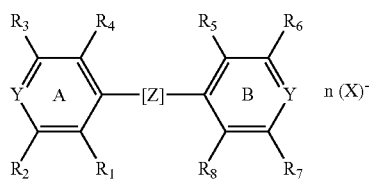

wherein:

Z is a 4-branched pyridiniumyl radical substituted by two aryl groups, a N-alkylpyridinium group or fused with at least one 1,2,3,4-tetrahydronaphthalene system;

each Y is independently selected from (⁺N—R₉)(X⁻) with R₉ a $C_3$-$C_{18}$ alkyl, a N-alkylpyridinium group or an aryl;

each one of $R_1$-$R_8$ is independently selected from H, alkyl, alkoxy, alkylthio, haloalkyl, haloalkoxy, haloalkylthio, polyalkylenoxy, alkoxycarbonyl, aryl or heteroaryl;

n is 1, 2, 3 or 4; and

X⁻ is a counterion.

2. The compound according to claim 1, wherein Y is (⁺N—R₉)(X⁻) where R₉ a $C_6$-$C_8$ alkyl, a N—$C_3$-$C_{18}$ alkylpyridinium or a phenyl.

3. The compound according to claim 1, wherein each one of $R_1$-$R_8$ is H.

4. The compound according to claim 1, wherein the counterion X⁻ is selected from the group consisting of halide, tetrafluoroborate, tetraphenylborate, hexafluorophosphate, nitrate, methanesulfonate, trifluoromethane sulfonate, toluene sulfonate, hexachloroantimonate, bis(trifluoromethanesulfonyl)imide, perchlorate, acetate and sulfate.

5. The compound according to claim 1, wherein said compound is selected from the group consisting of:

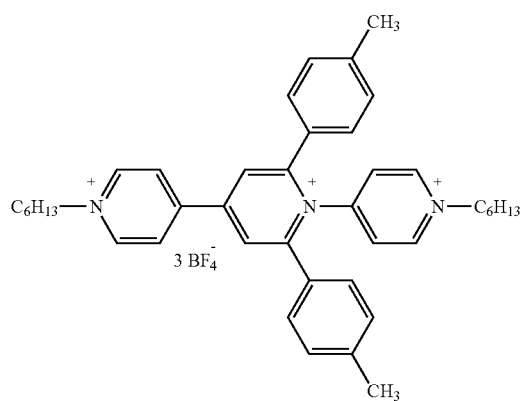

-continued
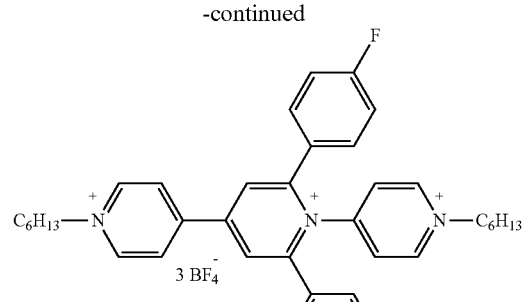
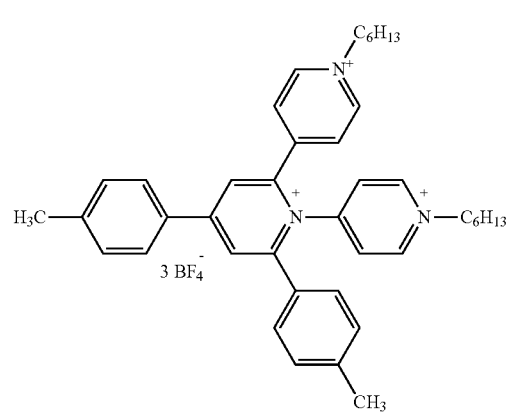
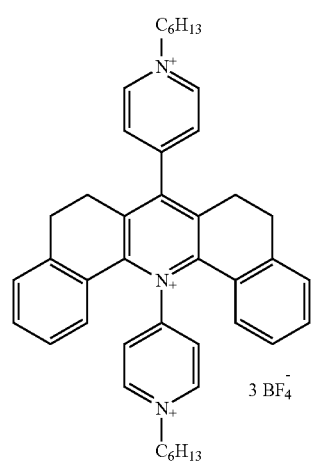
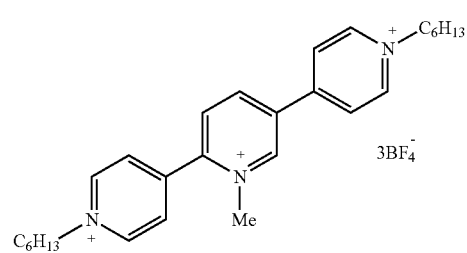
-continued
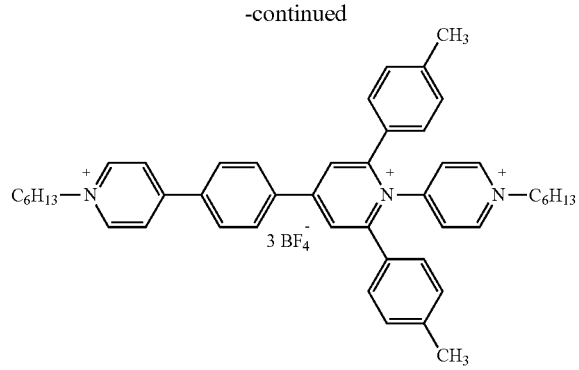
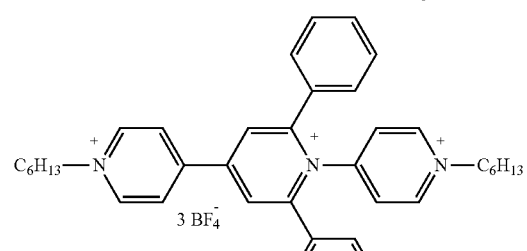
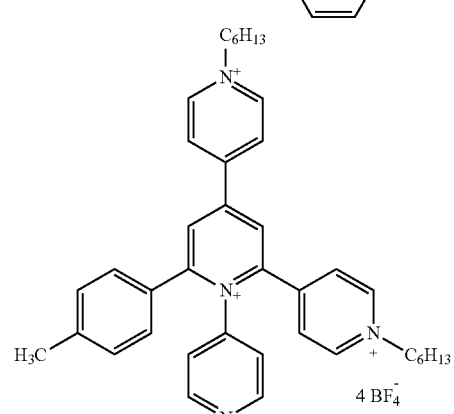
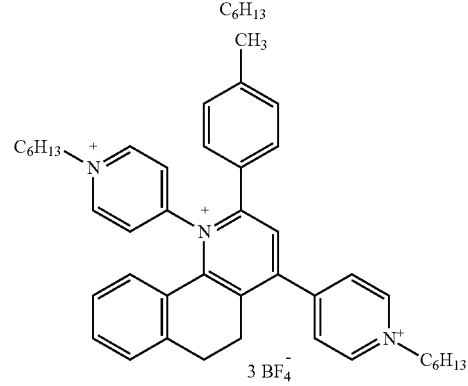
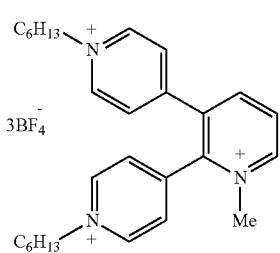

-continued

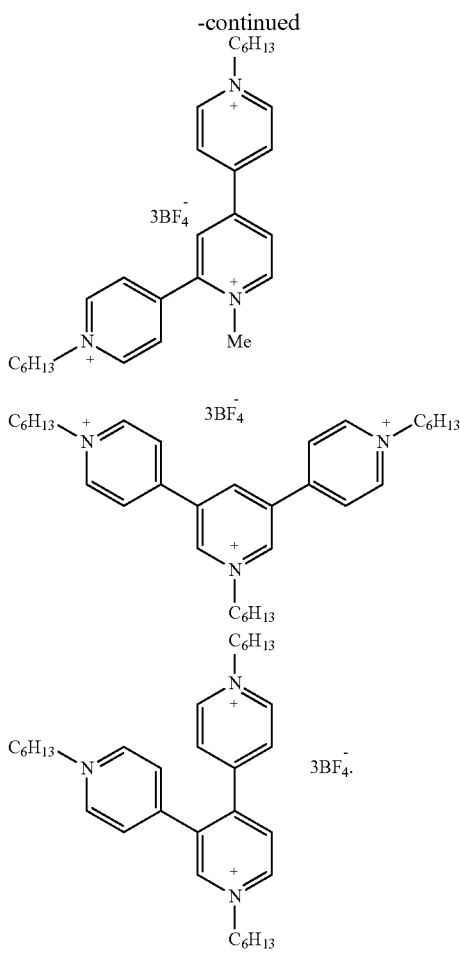

6. The compound according to claim 1, wherein said compound shows one redox potential such that the redox reaction is reversible or at least two redox potentials such that the potential difference between the said redox potential is above 0.1 V.

7. The compound according to claim 6, wherein the intensity of the second redox potential is lower than the intensity of the first one.

8. An electrochromic composition comprising at least one compound of formula (I) according to claim 1.

9. The electrochromic composition according to claim 8, wherein said composition further comprises a host medium.

10. The electrochromic composition according to claim 9, wherein the host medium is selected from the group consisting of organic solvents, liquid crystals, polymers, liquid crystal polymers, and mixtures thereof.

11. An electrochromic device comprising a compound according to claim 1.

12. The electrochromic device according to claim 11, wherein said device comprises a mechanism for holding said compound or said composition in a mechanically stable environment.

13. The electrochromic device according to claim 11, wherein said device comprises a pair of opposed substrates having a gap there between for receiving said compound or said composition, and a frame for holding said pair of substrates adjacent one another.

14. The electrochromic device according to claim 11, wherein said device comprises an optical component provided with at least one transparent cell arrangement juxtaposed in a parallel direction to the surface thereof, each cell being tightly closed and comprising said compound or said composition.

15. The electrochromic device according to claim 11, wherein said electrochromic device is selected from the group consisting of an optical article, a window, a visor, a mirror and a display.

* * * * *